US009464121B2

(12) United States Patent
Romero Mejia et al.

(10) Patent No.: US 9,464,121 B2
(45) Date of Patent: Oct. 11, 2016

(54) COMPOSITIONS AND METHODS FOR TREATING ERECTILE DYSFUNCTION

(75) Inventors: Fernando Gonzalo Romero Mejia, Temuco (CL); Raul Patricio Salvatici Salazar, Temuco (CL); Antonio Miranda, Sao Paulo (BR)

(73) Assignees: UNIVERSIDAD DE LA FRONTERA, Temuco (CL); UNIVERSIDAD FEDERAL DE SAO PAULO, Sao Paulo (BR); LABORATORIOS ANDROMACO S.A., Penalolen, Santiago (CL)

( * ) Notice: Subject to any disclaimer, the term of this patent is extended or adjusted under 35 U.S.C. 154(b) by 1534 days.

(21) Appl. No.: 12/811,021

(22) PCT Filed: Dec. 31, 2008

(86) PCT No.: PCT/IB2008/003977

§ 371 (c)(1), (2), (4) Date: Oct. 1, 2010

(87) PCT Pub. No.: WO2009/083808

PCT Pub. Date: Jul. 9, 2009

(65) Prior Publication Data

US 2011/0021445 A1 Jan. 27, 2011

(30) Foreign Application Priority Data

Dec. 31, 2007 (CL) .................................. 3884/2007

(51) Int. Cl.

| | |
|---|---|
| ***C07K 14/00*** | (2006.01) |
| ***A61K 38/16*** | (2006.01) |
| ***C07K 14/435*** | (2006.01) |
| *A61K 35/646* | (2015.01) |

(52) U.S. Cl.

CPC ....... *C07K 14/43518* (2013.01); *A61K 35/646* (2013.01)

(58) Field of Classification Search

CPC ....................... C07K 14/43518; A61K 35/646

See application file for complete search history.

(56) References Cited

U.S. PATENT DOCUMENTS

| | | | | |
|---|---|---|---|---|
| 6,204,383 | B1 | 3/2001 | Lu et al. | |
| 2003/0194704 | A1* | 10/2003 | Penn et al. | 435/6 |

FOREIGN PATENT DOCUMENTS

| | | |
|---|---|---|
| WO | 95/29235 | 11/1995 |
| WO | 01/40290 | 6/2001 |

OTHER PUBLICATIONS

Romero et al. Veneno de Latrodectus mactans de Chile (Araneae, Therididae): su efecto sobre músculo liso. Rev. biol. trop vol. 51 No. 2, pp. 305-312. Jun. 2003. Machine translation included as pp. 1-9.*

Uniprot Protein Database, protein Accession Q4U4N3, Alpha-Latrotoxin-associated low moleculer weight protein-2, accessed on Nov. 20, 2015, sequence published online in 1987.*

Cardoso et al., "Molecular cloning and characterization of Phoneutria nigriventer toxins active on calcium channels," Toxicon., 41(7):755-763 (2003).

Cestele et al., "Molecular mechanisms of neurotoxin action on voltage-gated sodium channels," Biochimie , 82(9-10):883-892 (2000).

Database Accession No. Q4U4N3, Retrieved from EBI, Jul. 5, 2005.

Dulubova et al., "Cloning and structure of delta-latroinsectotoxin, a novel insect-specific member of the latrotoxin family: functional expression requires C-terminal truncation," J. Biol. Chem., 271(13):7535-7543 (1996).

Filippov et al., "Mechanism of alpha-latrotoxin action as revealed by patch-clamp experiments on Xenopus oocytes injected with rat brain messenger RNA," Neuroscience, 61(1):179-189 (1994).

Fletcher et al., "The structure of versutoxin (delta-atracotoxin-Hv1) provides insights into the binding of site 3 neurotoxins to the voltage-gated sodium channel," Structure, 5(11):1525-1535 (1997).

Grasso, "Preparation and properties of a neurotoxin purified from the venom of black widow spider (Latrodectus mactans tredecimguttatus)," Biochim. Biophys. Acta., 439(2):406-412 (1976).

Henkel et al., "Mechanisms of alpha-latrotoxin action," Cell Tissue Res., 296(2):229-233 (1999).

Ichtchenko et al., "alpha-latrotoxin action probed with recombinant toxin: receptors recruit alphalatrotoxin but do not transduce an exocytotic signal," EMBO J., 17(21):6188-6199 (1998).

International Search Report issued in PCT/IB2008/003977 on Nov. 23, 2009.

Kiyatkin et al., "Cloning and structural analysis of alpha-latroinsectotoxin cDNA. Abundance of ankyrin-like repeats," Eur. J. Biochem., 213(1):121-127 (1993).

Knipper et al., "Black widow spider venom-induced release of neurotransmitters: mammalian synaptosomes are stimulated by a unique venom component (alpha-latrotoxin), insect synaptosomes by multiple components," Neuroscience, 19(1):55-62 (1986).

Kovalevskaia et al., "[Identification and isolation of the protein insect toxin (alpha-latroinsectotoxin from venom of the spider Latrodectus mactans tredecimguttatus]," Bioorg. Khim., 16(8):1013-1018 (1990) (with English-translated Abstract).

Krasnoperov et al., "[A crustacean-specific neurotoxin from the venom of the black widow spider Latrodectus mactans tredecimguttatus]," Bioorg. Khim., 16(11):1567-1569 (1990) (with English-translated Abstract).

Krasnoperov et al., "[Isolation and properties of insect-specific neurotoxins from venoms of the spider Lactodectus mactans tredecimguttatus]," Bioorg. Khim., 16(8):1138-1140 (1990) (with English-translated Abstract).

(Continued)

*Primary Examiner* — James H Alstrum Acevedo
*Assistant Examiner* — Erinne Dabkowski
(74) *Attorney, Agent, or Firm* — Lucas & Mercanti, LLP

(57) ABSTRACT

The present invention features compositions and methods for the treatment of erectile dysfunction. The compositions include substantially pure polypeptides derived from α-latrotoxin and can include other substances, such as pharmaceutically acceptable carriers or diluents, liposomes, hydrogels, and additional active ingredients for the treatment of erectile dysfunction. Also provided are methods, including methods for using the compositions for treatment of erectile dysfunction and in the preparation of medicaments.

6 Claims, 13 Drawing Sheets

(56) References Cited

OTHER PUBLICATIONS

Krasnoperov et al., "Structural requirements for alpha-latrotoxin binding and alpha-latrotoxin-stimulated secretion. A study with calcium-independent receptor of alpha-latrotoxin (CIRL) deletion mutants," J. Biol. Chem., 274(6):3590-3596 (1999).

Leite et al., "Targets for the treatment of erectile dysfunction: is NO/cGMP still the answer?" Recent Pat. Cardiovasc. Drug Discov., 2(2):119-132 (2007).

Magazanik et al., "Selective presynaptic insectotoxin (alpha-latroinsectotoxin) isolated from black widow spider venom," Neuroscience, 46(1):181-188 (1992).

Meldolesi et al., "The effect of alpha-latrotoxin on the neurosecretory PC12 cell line: studies on toxin binding and stimulation of transmitter release," Neuroscience, 10(3):997-1009 (1983).

Mintz et al., "P-type calcium channels blocked by the spider toxin omega-Aga-IVA," Nature, 355(6363):827-829 (1992).

Musicki et al., "In vivo analysis of chronic phosphodiesterase-5 inhibition with sildenafil in penile erectile tissues: no tachyphylaxis effect," J. Urology, 174: 1493-1496 (2003).

NIH Consensus on Impotence, J. Am. Med. Assoc., 270:83-90 (1993).

Peterson, "Black widow spider envenomation," Clin. Tech. Small Anim. Pract., 21(4):187-190 (2006).

Rash et al., "Pharmacology and biochemistry of spider venoms," Toxicon., 40(3):225-254 (2002).

Swartz et al., "An inhibitor of the Kv2.1 potassium channel isolated from the venom of a Chilean tarantula," Neuron, 15(4):941-949 (1995).

Szeto et al., "Isolation and pharmacological characterisation of delta-atracotoxin-Hvlb, a vertebrate-selective sodium channel toxin," FEBS Lett., 470(3):293-299 (2000).

Tedford et al., "Scanning mutagenesis of omega-atracotoxin-Hv1 a reveals a spatially restricted epitope that confers selective activity against insect calcium channels," J. Biol. Chem., 279(42):44133-44140 (2004).

Teixeira et al., "Sequence and structure-activity relationship of a scorpion venom toxin with nitrergic activity in rabbit corpus cavernosum," FASEB J., 17(3):485-487 (2003).

Trifaro et al., "Monolayer co-culture of rat heart cells and bovine adrenal chromaffin paraneurons," In vitro Cell Dev. Biol., 26(4):335-347 (1990).

Ushkaryov et al., "The multiple actions of black widow spider toxins and their selective use in neurosecretion studies," Toxicon., 43(5):527-542 (2004).

* cited by examiner

COMPOSITIONS AND METHODS FOR TREATING ERECTILE DYSFUNCTION

CROSS-REFERENCE TO RELATED APPLICATIONS

This application is the U.S. national stage under 35 USC §371 of International Application Number PCT/IB2008/003977, filed on Dec. 31, 2008, which claims priority to Chilean Patent Application No. 3884/2007, filed on Dec. 31, 2007, with the Department of Industrial Property of Chile, the entire contents of which applications are hereby incorporated by reference.

TECHNICAL FIELD

This invention relates to therapeutically active polypeptides originally obtained from the Chilean spider *Latrodectus mactans* and methods for their purification and use in treating erectile dysfunction (ED).

BACKGROUND

With erectile dysfunction (ED), there is an inability to develop and maintain an erection for sexual intercourse. The condition may result from psychogenetic or organic causes that alter the patient's erectile response. Variations in intensity make erectile dysfunction and its incidence in the population difficult to define. Depending on the definition used, there are varying estimates of from 15 to 30 million affected men in the world. According to the National Ambulatory Medical Care Survey (NAMCS), in 1985, of every 1000 men in the United States who visited their doctor, about eight discussed erectile dysfunction. In 1999, that number almost tripled (to about 22 men per thousand), perhaps because treatments were beginning to be released and discussion about erectile dysfunction began to be more accepted. The most publicised treatment has been the oral medication sildenafil citrate (Viagra®) (see, e.g., U.S. Pat. No. 6,204,383). NAMCS data indicates that Viagra® was mentioned about 2.6 million times during medical visits in 1999, and a third of those visits were for diagnostic reasons unrelated to ED.

The erection process requires a sequence of events and ED can occur when any of these is interrupted. The required events include nerve impulses in the brain, spinal cord, and area around the penis, and various responses in muscles, fibrous tissues, veins, and arteries in and near the corpus cavernosa. Erectile dysfunction is sometimes associated with a disease such as diabetes, kidney disease, chronic alcoholism, multiple sclerosis, arteriosclerosis, vascular disease or neurological disease, but it can also be a side effect of medication (e.g., a side effect of an antihypertensive, an antihistamine, antidepressant, tranquilizer, appetite suppressant, or cimetidine). Other causes include trauma, including surgery (in particular, prostate surgery) that results in nerve damage or restricts blood flow to the penis. In the absence of any organic cause, ED may be determined to be of psychological origin (PED), due to depression, anxiety, stress, tension, or guilt. ED is not a normal consequence of aging, but its incidence does increase with age. About 5% of 40-year-old men and between 15 and 25% of 65-year-old men experience ED. Successful treatment can occur at any age.

Standard drug treatments for ED include a class of drugs known as phosphodiesterase 5 (PDE-5) inhibitors (e.g., sildenafil citrate (Viagra®)). Although these drugs can be very effective, about 30% of all patients treated are refractile to their effects. The PDE5 inhibitors are associated with side effects including headache, flushing, upset stomach, stuffy nose, urinary tract infection, visual changes such as mild and temporary changes in blue/green colors or increased sensitivity to light, and diarrhea. Moreover, these drugs are contraindicated in patients who are taking nitrate drugs for angina, such as nitroglycerin (Nitro-Bid™ and others), isosorbide mononitrate (Imdur™) and isosorbide dinitrate (Isordil™); anticoagulants, and certain types of alpha blockers for enlarged prostate (benign prostatic hyperplasia) or high blood pressure. The PDE5 inhibitors may not be suitable for patients who have severe heart disease, heart failure, hypotension, hypertension, uncontrolled diabetes or who have had a stroke, or for those patients with haematological disorders that may be associated with priapism (e.g., anaemia of falciform cells, multiple myeloma or leukaemia). Accordingly, there is a continuing need for safe and effective therapies for treatment of ED.

SUMMARY

The present invention features compositions and methods that can be used, inter alia, to treat erectile dysfunction. The compositions include a polypeptide isolated from the venom of the black widow spider, *Latrodectus mactans*, and biologically active fragments or other variants thereof. Thus, the present polypeptides can be derived from a latrotoxin (e.g., an alpha-latrotoxin) which may be, for example, a latrotoxin precursor protein, mature latrotoxin, a latrotoxin-associated protein or a biologically active fragment, other variant, or homolog thereof. The latrotoxin precursor protein includes the mature latrotoxin sequence, and one or more of the present polypeptides may lie partially or wholly within the mature latrotoxin (e.g., alpha-latrotoxin) sequence. The biologically active fragments and other polypeptide variants encompassed by the invention will have sequences that differ from a naturally occurring latrotoxin or from a reference sequence (e.g., SEQ ID NO:1) by a certain limited extent but retain the ability to function (e.g., retain sufficient activity to be used for one or more of the purposes described herein).

The polypeptides, nucleic acids, and host cells described herein can be formulated in various ways and can include pharmaceutically acceptable carriers. Accordingly, the invention features physiologically acceptable compositions that are ready for administration as well as concentrated stocks or lyophilized powders of the present polypeptides. Formulations that are ready for use and those that require further manipulation (e.g., dilution or suspension) can be packaged as kits with instructions for use and, optionally, any device or implement that may facilitate administration. While the sequences of the present polypeptides can vary, useful polypeptides include those that are at least 80% identical to SEQ ID NO:1: GDSLDPAEFACADDID QAELLKNNDICLQCEDLHKEGLVFSLCKTNCFSTEY-FQHCVKDLEEAKKEPPE (SEQ ID NO:1). In some embodiments, the present polypeptides specifically exclude those that consist of or include the sequence represented by SEQ ID NO:2, which is also known as α-latrotoxin-associated protein 2, (Genbank number AAY33774; GI:63109347) and has the amino acid sequence: MLKLICIAFL VTV-LTLVAGQ DSLDPAEFGC ADDVNQAELL KNNDI-CLQCE DLHKEGVVFS LCKTNCFTTE YFQHCVKDLE EAKKEPPE (SEQ ID NO:2; the contiguous sequence shown here in 10-amino acid blocks).

The amino acid sequence of the present polypeptides can vary from SEQ ID NO:1 by virtue of containing (or containing only) one or more amino acid substitutions, insertions, or deletions. The substitutions may be considered conservative, such as a substitution within the following groups: glycine and alanine; valine, isoleucine, and leucine; aspartic acid and glutamic acid; asparagine, glutamine, serine and threonine; lysine, histidine and arginine; and phenylalanine and tyrosine. Non-conservative substitutions may also be made and non-naturally occurring amino acids can also be incorporated. Alternatively, or in addition, the amino acid sequence can vary from SEQ ID NO:1 (which may be considered the "reference" sequence) by virtue of containing an insertion and/or deletion of one or more amino acid residues.

More specifically, the polypeptides of the invention can include or consist of the amino acid sequence represented by SEQ ID NO:1. Also within the scope of the invention are polypeptides that are at least 70% identical to SEQ ID NO:1 (e.g., at least 80, 85, 87, 90, 95, 97, or 98% identical). In some embodiments, the present polypeptides exclude the polypeptide comprising or consisting of the amino acid sequence of SEQ ID NO:2.

Nucleic acid molecules that encode the present polypeptides are also within the scope of the invention. The nucleic acids are useful, for example, in making the polypeptides of the present invention and as therapeutic agents. They may be administered to cells in culture or in vivo and may include regulatory sequences (e.g., a promoter, which may be tissue-specific) and sequences encoding a secretory signal that directs or facilitates secretion of the polypeptides from a cell. While we may refer to the nucleic acids as "isolated," we note that the present nucleic acids may include non-naturally occurring sequences and would be, by virtue of that, distinguished from nucleic acids in their natural setting. Similarly, while we may refer to the polypeptides as "purified" (or "substantially pure"), where the polypeptides differ from a naturally occurring polypeptide, they are distinguished from naturally occurring polypeptides on that basis (and some degree of purity is therefore not required for patentability).

As noted, recombinant vectors (or "constructs") and host cells are also provided. A recombinant vector can include a nucleotide sequence encoding any of the presently described polypeptides, and those sequences can be operably linked to one or more regulatory regions within the vector suitable for use in either a prokaryotic or a eukaryotic expression system (many of which are known in the art). The regulatory region can be, for example, a promoter. Useful promoters include cell type-specific promoters, tissue-specific promoters, constitutively active promoters and broadly expressing promoters. The host cells can be bacterial, fungal, insect, plant or mammalian cells including such nucleic acid constructs.

The polypeptides can be formulated as pharmaceutical compositions in any pharmaceutically acceptable medium. Carriers and stabilizing agents may be added to facilitate drug delivery and to insure shelf-life. Formulations can be tailored to the route of administration and can include ingredients suitable for, for example, oral, parenteral, pulmonary, topical or transdermal or transmucosal administration. For example, encapsulation of the polypeptides in a suitable delivery vehicle (e.g., polymeric microparticles or implantable devices) may increase the efficiency of delivery.

The compositions (e.g., the pharmaceutical compositions) can include a second pharmaceutically active ingredient. The second pharmaceutically active ingredient can be another agent that is useful for the treatment of ED (e.g., a PDE5 inhibitor (e.g., sildenafil citrate)). The compositions of the invention are not so limited, however, and also encompass other agents such as prostaglandins, hormones (e.g., testosterone), apomorphine, melanocortin activators, and/or yohimbine.

The methods of the invention include methods for treating a subject (e.g., a human patient) with a condition associated with dysfunctional smooth muscle (e.g., erectile dysfunction). These methods can include the steps of a) identifying a subject who is experiencing or is likely to experience erectile dysfunction; and b) providing to the subject a composition including a latrotoxin polypeptide or biologically active variants of a latrotoxin polypeptide (e.g., a substantially pure polypeptide comprising an amino acid sequence that is at least 80% identical to SEQ ID NO:1).

The compositions can be administered to a subject in a variety of ways. For example, the compositions can be administered intravenously, intramuscularly, subcutaneously, transdermally or transmucosally, orally, parenterally, subcutaneously, intraperitoneally, or intrapulmonarily. The dosage required will depend upon various factors typically considered by physicians. These factors include the route of administration, the nature of the formulation, the nature of the patient's underlying illness, if any, the subject's size, weight, surface area, age, gender, other drugs being administered to the patient, and the judgment of the attending physician. Suitable dosages are in the range of 0.01-100.0 μg/kg. The compositions can be administered along with or in addition to other treatments for erectile dysfunction (e.g., medical devices, surgery or psychotherapy).

The latrotoxin polypeptides can also be used in the preparation of a medicament; the medicament can be used for the treatment of erectile dysfunction. Polypeptides amenable to such use include substantially pure polypeptides comprising an amino acid sequence that is at least 80% identical to SEQ ID NO:1. In some embodiments, the amino acid sequence of the polypeptide is not SEQ ID NO:2. Other useful polypeptides include those in which the amino acid sequence varies from SEQ ID NO:1 by virtue of containing one or more amino acid substitutions, which may or may not include conservative amino acid substitutions, and/or one or more amino acid deletions or insertions. The polypeptides used in the preparation of the medicament can comprise or consist of an amino acid sequence that is at least 85%, at least 90%, at least 95%, or at least 98% identical to SEQ ID NO:1 (e.g., 100% identical to SEQ ID NO:1).

A method of making the latrotoxin polypeptides of is also within the scope of the present invention. For example, the method includes culturing host cells for a time and under conditions appropriate for expression of any of the present polypeptides, followed by isolation of the polypeptides from the host cells or the medium in which the host cells were cultured.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
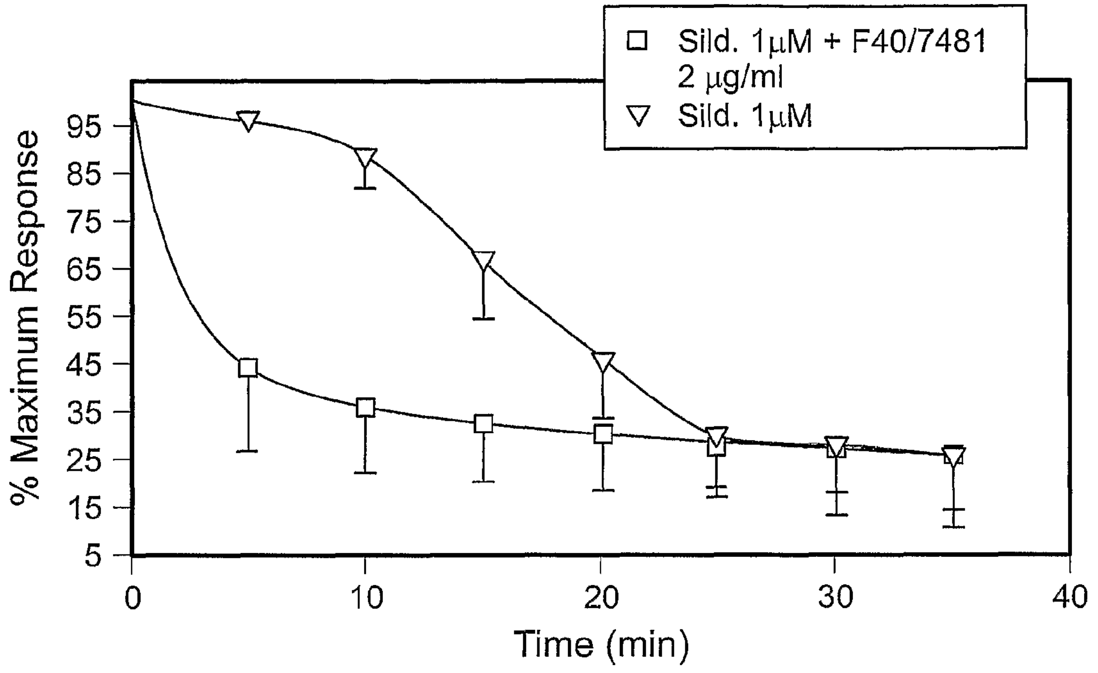
FIG. 1 depicts a graph comparing the effect of sildenafil citrate on corpus cavernosum relaxation in the presence (■) and absence (▲) of F40/7481 (SEQ ID NO:1) at a concentration of 2 μg/ml.

The present invention is based, in part, on our discovery of a polypeptide isolated from the Chilean spider, *Latrodectus mactans*. The polypeptide and biologically active fragments and other variants thereof are useful in the treatment of conditions such as erectile dysfunction. The polypeptide, designated in the experiments described below as "f40/7481" has a molecular weight of about 7.5 kDa, six cysteine residues, which may form three internal disulfide bonds, and the amino acid sequence: GDSLDPAEFA CADDIDQAEL LKNNDICLQC EDLHKEGLVF SLCKTNCFST EYFQHCVKDL EEAKKEPPE (SEQ ID NO:1; the contiguous sequence being shown here in 10-amino acid blocks).

The polypeptide and pharmaceutically acceptable compositions that include it have a myorelaxing effect on smooth muscle, for example, corpus cavernosum, and so are useful in treating conditions in which smooth muscle relaxation is problematic. For example, the present polypeptides can be used in the treatment of erectile dysfunction. While the present compositions are not limited to those that exert their effect by any particular cellular mechanism, our working hypothesis is that, with respect to erectile dysfunction, the effects of the polypeptides are mediated by NO via a cholinergic pathway. Moreover, the pathway does not appear to involve calcium mobilization.

Polypeptides:

It is known in the art that some poisons or toxins can elicit an erection. For example, an alfatoxin (MW 7,427 Da) isolated from the scorpion *Tytus serrulatus* (Teixeira et al., 2003) appears responsible for the release of NO to the corpus cavernosum in rabbits and induces penile relaxation and erection. In addition, from the *Latrodectus mactans tredecimguttatus* spider (Grasso A., 1976; Krasnoperov V G. et al., 1990; Kovalevskaia G I. et al., 1990, WO9529235), three fractions of high molecular weight alfa-latrotoxine (α-LTX), specific for vertebrates (Knipper M. et al., 1986; see also Meldolesi J. et al., 1983; Magazanik L G. et al., 1992 (in insects), Henkel et al., 1999; Ichtchenko et al., 1998, Krasnoperov et al., 1999; Dulubova et al., 1996); alfa-205 insectotoxine (α-LIT), specific for insects (Kiyatkin, N. et al., 1993) and alfa-125 latrocrustotoxine (α-LCTX), specific for crustacean (Krasnoperov V G. et al., 1990) were identified, sequenced and cloned. Toxins of specific activity against mammalian tissues have been isolated from spider samples (Rach et al. 2002).

The sequence of the 69 amino acid polypeptide obtained by the inventors from the Chilean *Latrodectus mactans* spider showed a relatively high decree of sequence conservation (78.41%) with polypeptides from another *Latrodectus* species, *L. mactans tredecimguttatus*. However, the differences in its structure suggest the polypeptide may have different and new pharmacologic properties compared to those described for the polypeptides in WO 95/29235.

Polypeptides from other spiders have been shown to have distinctive pharmacological properties. Three polypeptides with molecular weights of 4973, 4993 and 5159 Da were obtained from *Segestria florentina* spider from middle Asia. The first one had a synaptic transmission neuroblocking effect on the action of glutamate receptors, the second induced modulation on the pre- or postsynaptic terminals, and the third acted on the presynaptic terminals. Because these peptides cause paralysis in the insects preyed upon by the spinder, they have been porposed as potential insecticides.

Cytotoxin which block other ionic channels in a general manner have been obtained from other spider species, but these toxins do not have an effect on smooth muscle relaxation and so do not have erectile properties. For example, Cardoso et al., 2003, isolated polypetide fractions from *Phoneutria nigriventer* which allowed them to identify and characterize the molecular constitution of different families of ionic channels and define their evolutionary relationships. Filipov et al, 1994, showed that extopic expression of α-LTX receptors in Xenopus laevis oocytes resulted in the formation of ion channels with flux of over 10 pS of $Ca^{2+}$.

The N-Atracotoxin (N-ACTXs) is a polypeptidic toxin isolated from an Australian spider species, *Hadronyche versuta*, that acts on slow $Na^+$ ionic channels, in a manner similar to that of toxins obtained from the scorpions *Leirus quinquestriatus hebraeus* and *Androctonus euatralis hector* scorpions (Szeto et al., 2000) From the *Agelenopsis aperta* spider poison (Mintz et al., 1992; Cestele et al., 2000; Tedford et al., 2004) polypetides were isolated that had a $Ca^{2+}$ channel blocking activity on presynaptic terminals in insects neuron and in dendritic terminals of Purkinje neuron in rats brains; the active polypeptide was designated ω-Aga-IVA, of molecular mass 6051 Da. of 48 basis pairs. Others have also identified $Ca^{2+}$ channels blockers of the T/Q type from this spider species, while from the *Grammastola spatulata* species polypeptides that block voltage dependent $K^+$ channels have been identified (Swartz et al., 1995 and Fletcher et al., 1997). In 2004, Suchyna from the University of Buffalo identified a protein contained in the poison of the Chilean tarantula *Phyxotrichus Rosea*, that can block the action of ionic channels, which open and close when the cell collapse or gets narrower. Its action is associated with such diverse functions as the sense of touch, audition, blood pressure and muscular coordination and contraction, evidencing therapeutical properties of anti-arrthymics.

The Chilean spider, *Latrodectus mactans*, belongs to the genus *Latrodectus*. Its venom contains a rich cocktail of latrotoxins and other biologically active substances that affect the nervous system of victims. When bitten, humans experience severe abdominal pain, shivering, fever, vomiting, tachycardia, arterial hypertension, and priapism; deaths have been reported in both children and adults. To date, the venom has been found to contain seven proteins with neurotoxic activity, including five insectotoxins (α, β, γ, δ, and ϵ-LIT), one latrocrustatoxin, α-LCT (120 kDa), and one vertebrate toxin, α-LTX (130 kDa). In addition, two low molecular weight proteins (known as LMWPs) that usually co-purify with α-LTX have been identified and cloned. LMWPs are structurally related to crustacean hyperglycemic hormones and have molecular masses of 8 and 9.5 kDa. Latrotoxins exert their toxic effects in part by forming tetrameric complexes that insert into lipid membranes of cells and act as calcium permeable pores that result in massive release of neurotransmitters from the nerve terminals.

The terms "polypeptide" and "peptide" are used herein to refer to a compound of two or more subunit amino acids, amino acid analogs, or other peptidomimetics, regardless of post-translational modification (e.g., amidation, phosphorylation or glycosylation). The subunits can be linked by peptide bonds or other bonds such as, for example, ester or ether bonds. The term "amino acid" refers to natural and/or unnatural or synthetic amino acids, which may be D- or L-form optical isomers.

The present polypeptides, biologically active fragments, and other variants thereof can be chemically synthesized, purified from natural sources, or purified from cells in which the polypeptide or a biologically active variant thereof is recombinantly produced. The methods required for peptide synthesis, expression and purification are well known in the art. For example, peptides can be chemically synthesized using standard f-moc chemistry and purified using high pressure liquid chromatography (HPLC). The polypeptides can be purified by any method known in the art, including without limitation, fractionation, centrifugation, and chromatography (e.g., gel filtration, ion exchange chromatography, reverse-phase HPLC and immunoaffinity purification).

The present polypeptides may be, but are not necessarily, substantially purified. The present polypeptides will be substantially pure when they have been separated from the components (e.g., cellular components) with which they were previously associated such that a composition in which they is contained is at least or about 60% (e.g., at least or about 70%, 80%, 90%, 95%, or 99%), by weight, the polypeptide of interest. In general, a substantially pure polypeptide will yield a single major band on a non-reducing polyacrylamide gel.

To produce a recombinant f40/7481 polypeptide or a biologically active fragment or variant thereof, a nucleic acid encoding the peptide can be ligated into an expression vector and used to transform a prokaryotic (e.g., bacteria) or a eukaryotic (e.g., insect, yeast, plant, or mammal) host cell. In general, nucleic acid constructs can include a regulatory sequence operably linked to a nucleic acid encoding the f40/7481 polypeptide. Regulatory sequences (e.g., promoters, enhancers, polyadenylation signals, or terminators) do not typically encode a gene product, but instead affect the expression of a nucleic acid sequence. Such transformed or transfected cells can then be used, for example, for large or small scale production of the polypeptide by methods known in the art. In essence, such methods involve culturing the cells under conditions suitable for production of the polypeptide and isolating the polypeptide from the cells or from the culture medium.

A construct can include a tag sequence designed to facilitate subsequent manipulations of the expressed nucleic acid sequence (e.g., purification or localization). Tag sequences, such as green fluorescent protein (GFP), glutathione S-transferase (GST), c-myc, hemagglutinin, β-galactosidase, or Flag™ tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

In bacterial systems, *Escherichia coli* can be used to express fragments of a f40/7481 polypeptide or biologically active variants thereof. For example, the *E. coli* strain DH10B (Invitrogen) can be transformed with the gram negative broad host range vector, pCM66 containing a nucleic acid sequence encoding a f40/7481 polypeptide. In another example, BL-21 cells can be transformed with a pGEX vector containing a nucleic acid sequence encoding a f40/7481 polypeptide. The transformed bacteria can be grown exponentially and then stimulated with isopropylthiogalactopyranoside (IPTG) prior to harvesting. In general, GST fusion polypeptides produced from a pGEX expression vector can be purified from lysed cells by adsorption to glutathione-agarose beads followed by elution in the presence of free glutathione. The pGEX vectors can be designed to include thrombin or factor Xa protease cleavage sites so that the expressed polypeptide (e.g., the f40/7481 polypeptide) can be released from the GST moiety.

The invention further encompasses peptidomimetics of the present polypeptides or fragments thereof, which are small, protein-like polymers containing non-peptidic structural elements that are capable of mimicking or antagonizing the biological actions of a natural parent peptide (here, a f40/7481 polypeptide). In addition to being synthetic, non-peptide compounds, peptidomimetics have a three-dimensional conformation (i.e., a "peptide motif") that is substantially the same as the three-dimensional conformation of a selected peptide. The peptide motif provides the peptidomimetic compound with the ability to bind the receptor in a manner qualitatively identical to that of the parent peptide from which the peptiomimetic was derived. Peptidomimetic compounds can have additional characteristics that enhance their therapeutic utility, such as an increased biological half-life.

The peptidomimetics typically have a backbone that is partially or completely non-peptide, but with side groups that are identical to the side groups of the amino acid residues that occur in the peptide on which the peptidomimetic is based. Several types of chemical bonds (e.g., ester, thioester, thioamide, retroamide, reduced carbonyl, dimethylene and ketomethylene bonds) are known in the art to be generally useful substitutes for peptide bonds in the construction of protease-resistant peptidomimetics and can be used in the context of the present polypeptides.

Any peptidomimetic that has a sufficient amount of biological activity (e.g., an amount that renders the peptide experimentally or clinically useful in lieu of f40/7481 polypeptide) can be used in the present methods.

Biologically active variants of the present polypeptides can include structural modifications. For example, one can chemically modify the peptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a fragment of a f40/7481 polypeptide can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

The polypeptides described herein can be chemically synthesized, purified from natural sources (insofar as they exist in those sources or can be obtained from naturally occurring proteins (by, for example, digestion)), or purified from cells in which the f40/7481 polypeptide or a biologically active variant thereof is recombinantly produced. The methods required for peptide synthesis, expression and purification are well known in the art. See for example, Kimmerlin and Seebach (*J. Pept. Res.* 65:229-260, 2005). For example, peptides can be chemically synthesized using standard f moc chemistry and purified using high pressure liquid chromatography (HPLC). Refined solid phase chemical synthesis techniques combined with fragment condensation and ligation methods, have allowed for the precise synthesis of peptides over 150 amino acids in length. Solid-phase peptide synthesis consists of three distinct sets of operations: 1) chain assembly on a resin; 2) simultaneous or sequential cleavage and deprotection of the resin-bound, fully protected chain; and 3) purification and characterisation of the target peptide. Various chemical strategies exist for the chain assembly and cleavage/deprotection operations, but purification and characterisation methods are more or less invariant to the methods used to generate the crude peptide product. Two major chemistries for solid phase peptide synthesis are Fmoc (base labile protecting group) and t-Boc (acid labile $\alpha$-amino protecting group). Each method involves fundamentally different amino acid side-chain protection and consequent cleavage/deprotection methods, and resins; t-Boc method requires use of stronger HF containing anisole alone or anisole plus other scavengers, where peptide-resins assembled by Fmoc chemistry usually cleaved by less harsh reagents K or R. Fmoc chemistry is known for peptide synthesis of higher quality and in greater yield than t-Boc chemistry. Impurities in t-Boc-synthesized peptides mostly attributed to cleavage problems, dehydration and t-butylation. For peptide assembly HBTU/HOBt, carbodiimidemediated coupling and PyBOP/HOBt are commonly used methods. Synthetic peptides are typically purified by reverse-phase HPLC (high performance liquid chromatography) using columns such as C-18, C-8, and C-4.

Nucleic Acids: The terms "nucleic acid" and "polynucleotide" may be used interchangeably to refer to either RNA or DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a f40/7481 polypeptide.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein (i.e. an f40/7481 polypeptide). PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making a biologically active variant of a fragment of an f40/7481 polypeptide).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of an f40/7481 polypeptide.

Two nucleic acids or the polypeptides they encode may be described as having a certain degree of identity to one another. For example, an f40/7481 polypeptide and a biologically active variant thereof may be described as exhibiting a certain degree of identity. Alignments may be assembled by locating short f40/7481 polypeptide sequences in the Protein Information Research (PIR) website followed by analysis with the "short nearly identical sequences" Basic Local Alignment Search Tool (BLAST) algorithm on the NCBI website.

One can determine the "percent sequence identity" by determining the degree of identity between any given query sequence and a subject or reference sequence. For example, one could make several mutations in the amino acid sequence represented by SEQ ID NO:1 and then determine the percent sequence identity between that mutant (the query sequence) and SEQ ID NO:1 (the subject or reference sequence) by aligning the sequences and counting the number of positions at which the query sequence differs from the reference sequence. For example, if one were to mutate SEQ ID NO:1 by removing one residue at each terminal and substituting two amino acids within the sequence, the query sequence would differ from the reference sequence at four positions and, therefore, be at least 94% (65/69) identical to the reference sequence.

To determine sequence identity in more complicated scenarios, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

The nucleic acids and polypeptides described herein may include heterologous nucleotides or amino acids, respectively. For example, the sequences can include nucleotides or amino acids that are not normally contiguous with the arachnid sequences, including sequences from another species.

Recombinant constructs are also provided herein and can be used to transform cells in order to express the present polypeptides. A recombinant nucleic acid construct comprises a nucleic acid encoding a polypeptide described herein, operably linked to a regulatory region suitable for expressing the fragment of an f40/7481 polypeptide in the cell. In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for an f40/7481 polypeptide can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs. YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.)

sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Methods of Treatment:

The polypeptides disclosed herein are generally useful in the prophylaxis and treatment of conditions in which an adverse event is caused by excessive smooth muscle contraction. These include conditions in which gastric motility is too high; urological or gynecological conditions such as overactive bladder or pelvic floor dysfunction; and erectile dysfunction. "Prophylaxis" means a symptom of a condition is ameliorated before the symptom is problematic. Thus, a prophylactic treatment may delay the onset of the symptom(s) of a condition or lessen the severity of a subsequently developed symptom. "Treatment" or "treating" is more usually applied to indicate that intervention occurs after a symptom is noticeable or problematic. As used herein, "therapy" can mean abolishment of the symptoms of a condition or a decrease in the frequency or severity of the symptoms of the condition following their onset.

The present methods may include a step in which a physician or other healthcare provider determines whether a subject is amenable to treatment. Accordingly, in the case of ED, the methods may include the step of identifying a patient who is unable to achieve functional erection, ejaculation, or both. ED is typically confirmed at least six months following a clinical diagnosis (see NIH Consensus on Impotence, *J. Am. Med. Assoc.* 270:83-90, 1993).

While the present methods are clearly intended for the treatment of humans, they may be used to treat animals in some instances. For example, they may be used to treat impotence in endangered animals or where offspring are particularly valued (e.g., the offspring of a racehorse). Administration and formulation: The polypeptides described herein can be administered to a mammal. Generally, the polypeptides can be suspended in a pharmaceutically acceptable carrier (e.g., physiological saline or a buffered saline solution) to facilitate their delivery. Encapsulation of the polypeptides in a suitable delivery vehicle (e.g., polymeric microparticles or implantable devices) may increase the efficiency of delivery. As with other protein or protein-based therapeutics, the polypeptides described herein may be administered within a hydrogel or lipid-based formulation. Methods of administering polypeptides in these ways are known in the art.

The polypeptides of the invention can be formulated in systems designed for delivery of peptide drugs including, but not limited to, biodegradable and nondegradable microspheres, liposomes, gel spheres, nano-spheres, niosomes, microcapsules, nanocapsules, injectable implants, diffusion-controlled hydrogels and other hydrophilic systems, microemulsions and multiple emulsions, and the use of iontophoresis or electroporation, macroflux transdermal patches.

Colonic drug delivery has gained increased importance not just for the delivery of the drugs for the treatment of local diseases associated with the colon but also for its potential for the delivery of proteins and therapeutic peptides. To maximize colonic delivery, a drug needs to be protected from absorption and/or the environment of the upper gastrointestinal tract (GIT) and then be abruptly released into the proximal colon.

The present compositions can be made by combining any of the polypeptides provided herein (or combinations thereof) with one or more pharmaceutically acceptable carriers. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present.

Regardless of their original source or the manner in which they are obtained, the polypeptides of the invention can be formulated in accordance with their use. For example, the polypeptides can be formulated within compositions for application to cells in tissue culture or for administration to a patient. When employed as pharmaceuticals, the present compositions can be prepared in any manner known in the pharmaceutical arts, and can be administered by a variety of routes, depending upon whether local or systemic treatment is desired and upon the area to be treated. Administration may be topical (including administration to mucous membranes including intranasal and rectal delivery as well as delivery to the skin covering the penis), pulmonary (e.g., by inhalation or insufflation of powders or aerosols, including by nebulizer; intratracheal, intranasal, epidermal and transdermal), ocular, oral or parenteral. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable. While oral or topical formulations are likely to be preferred, parenteral administration is feasible and includes intravenous, subcutaneous, intraperitoneal or intramuscular injection or infusion.

In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active polypeptides, soft and hard gelatin capsules, suppositories, sterile injectable solutions, and sterile packaged powders. As is known in the art, the type of diluent can vary depending upon the intended route of administration. The resulting compositions can include additional agents, such as preservatives. The polypeptides may also be contained within a pump, patch, or other drug delivery device. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formularly).

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The increasing use of synthesized or recombinantly expressed therapeutic proteins in the pharmaceutical industry has highlighted issues such as their stability during long-term storage and means of efficacious delivery that avoid adverse immunogenic side effects (Frakjaer and Otzen, *Nat. Rev. Drug Discov.* 4:298-306, 2005). To address these issues, controlled chemical modifications, such as substitutions, acylation and PEGylation have been employed and can be employed in the context of the polypeptides described here.

The compositions can be formulated in a unit dosage form, each dosage containing, for example, from about 0.01 mg to about 10 mg, 0.05 mg to about 20 mg, 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The present compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, between 7 and 8. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration.

The dosage required will depend on the route of administration, the nature of the formulation, the nature of the patient's illness, the patient's size, weight, surface area, age, and sex, other drugs being administered, and the judgment of the attending clinician. Suitable dosages can be in the range of 0.01-1,000 μg/kg Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the polypeptides in a suitable delivery vehicle (e.g., polymeric microparticles or implantable devices) may increase the efficiency of delivery.

The duration of treatment with any composition provided herein can be any length of time from as short as one day to as long as the life span of the host (e.g., intermittent treatment over the course of many years). For example, a polypeptide can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present polypeptides can be administered once daily or once, twice, three times, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Alternatively, a polynucleotide containing a nucleic acid sequence encoding a polypeptide can be delivered to an appropriate cell of the animal. This can be achieved by, for example, the use of a polymeric, biodegradable microparticle or microcapsule delivery vehicle, sized to optimize phagocytosis by phagocytic cells such as macrophages. For example, PLGA (poly-lactide-co-glycolide) microparticles approximately 1-10 μm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the engineered protein with an initiator methionine and optionally a targeting sequence is operatively linked to a promoter or enhancer-promoter combination. Promoters and enhancers are described above, and many are well known in the art. Polynucleotides can be administered in a pharmaceutically acceptable carrier. Pharmaceutically acceptable carriers are biologically compatible vehicles which are suitable for administration to a human or other mammalian subject (e.g., physiological saline). A therapeutically effective amount is an amount of the polynucleotide which is capable of producing a medically desirable result (e.g., a decrease in clinical motor symptoms) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Any method known to those in the art can be used to determine if a particular response is induced. For ED, patient reporting is useful along with clinical methods that can assess the degree of a particular disease state to determine if a response is induced. The particular methods used to evaluate a response will depend upon the nature of the patient's underlying disorder, the patient's age, and sex, other drugs being administered, and the judgment of the attending clinician. Some blood tests are generally done to exclude underlying disease, such as diabetes, hypogonadism and prolactinoma. Impotence is also related to generally poor physical health, poor dietary habits, obesity, and most specifically cardiovascular disease such as coronary artery disease and peripheral vascular disease. A useful and simple way to distinguish between physiological and psychological impotence is to determine whether the patient ever has an erection. If never, the problem is likely to be physiological; if sometimes (however rarely), it could be physiological or psychological. Examples of useful clinical tests for ED include duplex ultrasound, which can evaluate evaluate blood flow, venous leak, signs of atherosclerosis, and scarring or calcification of erectile tissue; penile nerves function; nocturnal penile tumescence (NPT); penile biothesiometry; penile angiogram; dynamic infusion cavernosometry; corpus cavernosometry; digital subtraction angiography; and magnetic resonance angiography (MRA).

Combination Therapies:

The polypeptides of the invention are useful when administered in pharmaceutical compositions either as a montherapy or along with other agents (e.g., other treatments for ED). The inventors have found a synergistic effect of the present polypeptide on the PDE5 inhibitor sildenafil citrate (Viagra®). Accordingly, the present compositions can include a PDE5 inhibitor and may result in a synergistic effect. That is, the combination of the two agents may result in a therapeutic effect equal to or greater than that achieved with a single dose of either agent given as a monotherapy and/or a greater therapeutic effect at a lower dose of one or more of the agents than would be achieved with a single agent given as monotherapy.

More specifically, the polypeptides of the invention can be administered in conjunction with other therapies for treating erectile dysfunction, such as standard, small molecule-type pharmaceutical agents, biopharmaceuticals (e.g., antibodies or antibody-related immunotherapies, siRNAs, shRNAs, antisense oligonucleotides and other RNA inhibitory molecules, microRNAs, and peptide therapeutics), surgery, or in conjuction with any medical devices that may be used to assist the patient. Unless the context indicates otherwise, we use the term "agent" to broadly refer to any substance that affects a target molecule (e.g., a ligand or the receptor to which it binds) or a target region of the body in a clinically beneficial way (e.g., to improve the ability of a subject to achieve and maintain an erection). For example, we may refer to chemical compounds such as sildenafil citrate as "agents". We may also use the term "compound" to refer to conventional chemical compounds (e.g., small organic or inorganic molecules). The "agent" may also be a protein or protein-based molecule, such as a mutant ligand or antibody. Other useful agents include nucleic acids or nucleic acid-based entities such as antisense oligonucleotides or RNA molecules that mediate RNAi and the vectors used for their delivery.

More specifically, the polypeptides of the invention can be administered along with pharmacological agents that act to increase and maintain high local concentrations of cGMP in the corpus cavernosum. Widely used therapies for ED accomplish this by inhibition of cGMP phosphodiesterase type 5 (PDE5), an enzyme that is responsible for the degradation of cGMP. Potent and selective inhibitors of PDE5 include, for example, Viagra™ (sildenafil), Cialis™ (tadalafil), and Levitra™ (vardenafil). The polypeptides of the invention can be administered along with a PDE5 inhibitor, for example, 1-[4-ethoxy-3-(6,7-dihydro-1-methyl-7-oxo-3-propyl-1H-pyrazolo[4,3-d]pyrimidin-5-yl) phenylsulfonyl]-4-methylpiperazine (sildenafil); (6R-trans)-6-(1,3-benzodioxol-5-yl)-2,3,6,7,12,12a-hexahydro-2-methyl-pyrazino[1',2':1,6]pyrido[3,4-b]indole-1,4-dione (tadalafil); or 4-[2-ethoxy-5-(4-ethylpiperazin-1-yl)sulfonyl-phenyl]-9-methyl-7-propyl-3,5,6,8-tetrazabicyclo [4.3.0]nona-3,7,9-trien-2-one (vardenafil). The combination of polypeptide and, for example, a PDE5 inhibitor, may result in a synergistic effect. That is, the combination of the two agents may result in a therapeutic effect equal to or greater than that achieved with a single dose of either agent given as a monotherapy and/or a greater therapeutic effect at a lower dose of one or more of the agents than would be achieved at with a single agent given as monotherapy. The polypeptide(s) and the other agents, for example, a PDE5 inhibitor can be administered concurrently or sequentially. In the case of concurrent administration the polypeptide and the PDE5 inhibitor can be formulated in a single pharmaceutical composition. In the case of sequential administration the polypeptide can be administered before or after the PDE5 inhibitor and the dosing can be separated by intervals of minutes, hours, days or weeks.

The polypeptides can also be administered to a patient who is receiving or who has received other treatments for ED. These include: prostaglandins (alprostadil), administered either by needle-injection or as an intrurethral suppository, hormone (e.g., testosterone) replacement therapy; vacuum inflation devices, penis pumps, vascular surgery, penile implants, Kegel exercises, psychological counseling and sex therapy.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Purification of the Polypeptide f40/7841

The f40/7481 polypeptide was purified from the raw poison obtained from female adult spiders of the Chilean species *Latrodectus mactans*. The spiders were fasted for 20 days in order to increase the concentration of toxin in the venom glands and then exposed to a cold environment (−20° C.) prior to harvest. The chelicerae (i.e., the mouth parts that contain the venom glands) were removed with tweezers and transferred to an Eppendorf tube containing a saline solution (PBS) (PBS: 0.1 mM $NaH_2PO_4$, 0.01 mM $NaHPO_4$, 1.35 mM NaCl, pH 7.4) and maintained at a temperature of −4° C. Each set of glands contained about 2 μl of venom. Samples were stored at −80° C. Crude extract was obtained by ultrasonic agitation, and debris was removed by centrifugation at −20° C. to 2000 rpm. This method illustrates methods of obtaining a crude extract of raw poison from spiders, which are within the scope of the present invention.

The crude extract was fractionated by HPLC chromatography. In the HPLC process, a Vydac C18 column was used (22×250), 300 Å, 15 m, with a solvent system composed of solvent A: 0.1% TFA/$H_2O$ and a solvent B: 60 ACN/A solvent, with elution in a 1-100% B in 99 minutes gradient, at a flow of 10 ml/min, at room temperature. Elution was monitored in a UV/visible detector at a wavelength of 220 nm.

All the fractions with protein concentrations greater than 0.2 mg/ml when freeze died were analysed in LC/MS. As described below, the fraction of interest was identified by in vitro (rat corpus cavernosum fragments) and in vivo assays (in mouse).

Fractions showing activity in vitro were then analysed through a mass spectrum a LC/ESI-MS Waters system, conformed by a separation module, Alliance model 2690, fotodyodic detector model 996, automatic injector with capacity for 120 samples and a Micromass spectometrum model 2 MD. The system was controlled by a Compaq model AP200. For the fractions that had the same retention time, or that had a similar chromatic profile and the same molecular weight determined by the mass detector (it was used physiologic screening), system that was controlled by a computing unit. The polypeptides (or the selected fraction of HPLC) were diluted in AcOH/$H_2O$ at 20%, to a concentration of 3 mg/ml. Samples were chromatographed on a C18 Waters Nova-Pak column (2.1×150) 60 Å, 3.5 m, with a solvent combination of an A solvent: 0.1% TFA/$H_2O$ and a B solvent: 0.1 TFA in 60% or 75% ACN/$H_2O$, using a gradient of 5% to 95% of B in 20 or 30 minutes, with a flow of 0.4 ml/min at a wavelength of 190-300 nm and a mass interval of 500-3930 daltons (Da).

Figure 4:
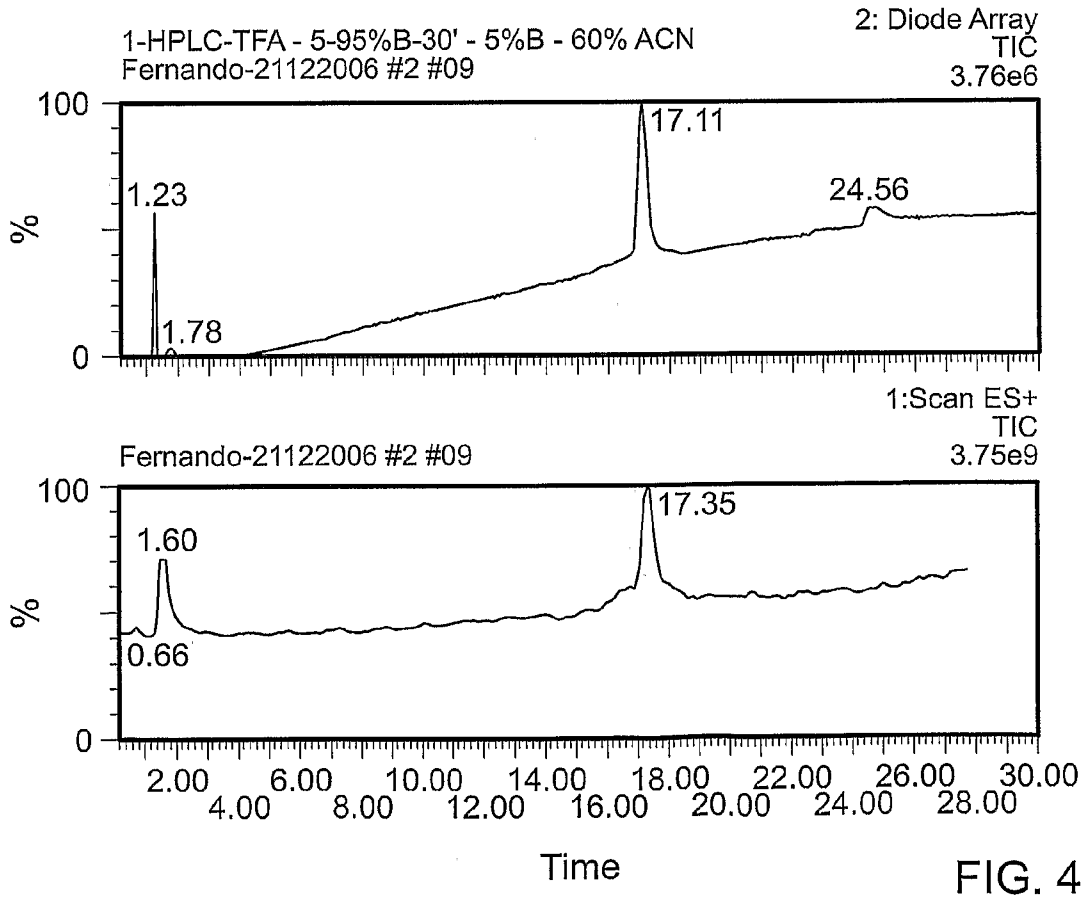
FIG. 4 depicts an HPLC chromatographic profile of the f40/7841 fraction shown in FIG. 3.

An HPLC/mass Waters chromatographic profile is shown in FIG. 4. Specific experimental conditions were Column: Waters Nova-Pak C18 (2.1×150 mm), 60 Å, 3.5 m; Solvents: A: 0.1% TFA/H2O B: 0.1% TFA en 60 ó 75% ACN/H2O Gradient: 5 a 95% de B en 20 ó 30 min. 855; Flow: 0.4 ml/min; Wavelength: 190-300 nm; Injected volume: 50 μL; Mass interval: 500-3930 Da; Mode: "Electrospray" Positive 860; Nitrogen flow: 4.1 L/h; Source temperature: 150° C.; Evaporation temperature: 400° C.; Cone voltage: 36 V; Energy in capillary: 4 kV 865; Extractor energy: 5 kV; Multiplier energy: 700 V; Low molecular weight resolution: 15.6; High molecular weight resolution: 8.7. FIG. 4 shows the profiles of purified extracts; the HPLC-MS strategy resulted in a unique compound with high purity corresponding to f40/7841 product. It can be clearly observed that the polypeptide eluted at 17.25 s and in the previous graphic corresponded to the expansion of the 1:1 s scale in a specimen analysis time of 30 s.

Figure 5:
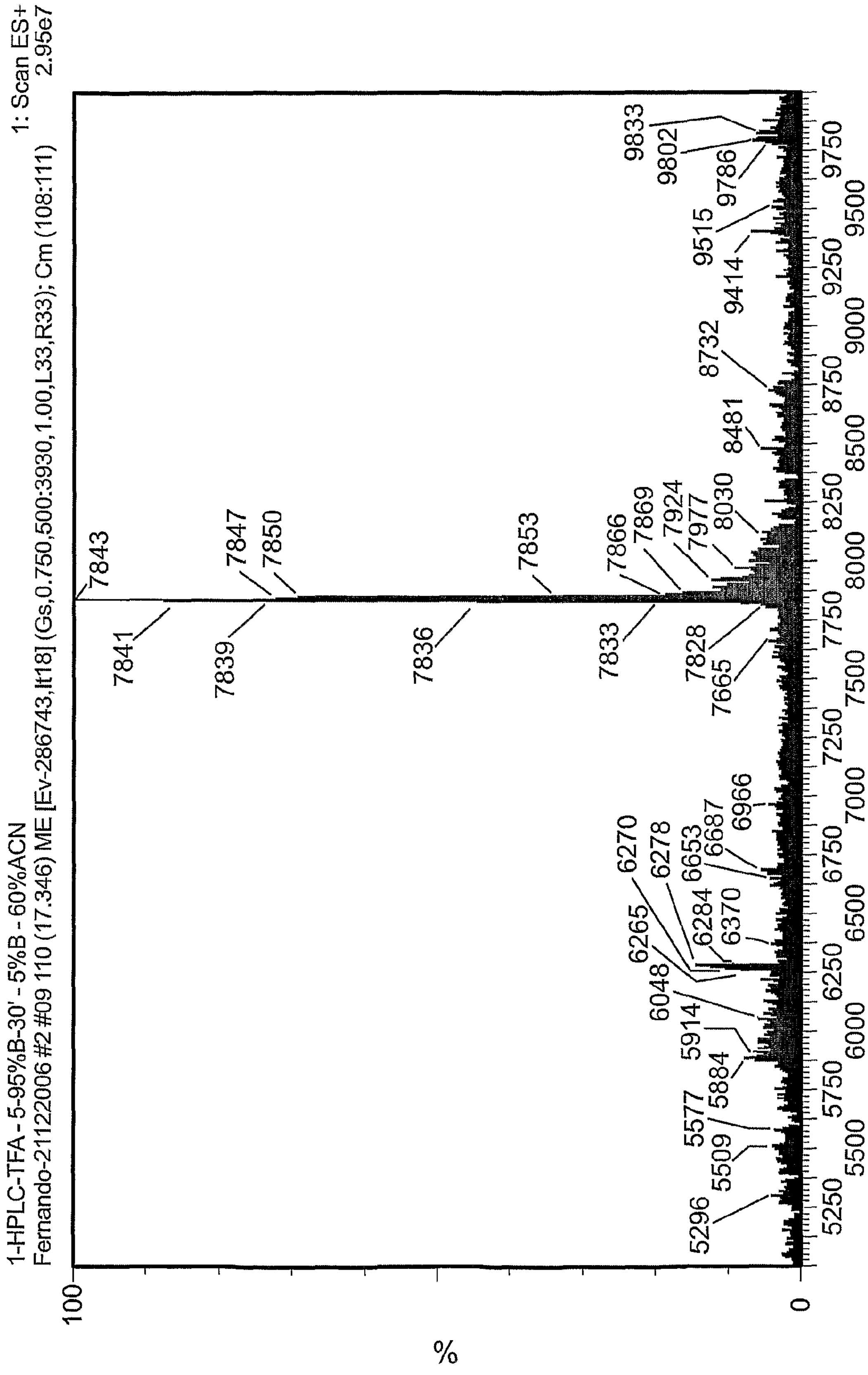
FIG. 5 depicts the molecular mass of the f40/7841 polypeptide.

The molecular mass of the fraction f40/7841 was consistent with the value obtained by HPLC. As shown in FIG. 5, the eluted polypeptide had a chromatographic profile of 7841 Da. The sequence of the polypeptide was determined by Edman degradation following deprotection of the blocked N-terminus with pyroglutamate aminopeptidase; the sequence was confirmed by HPLC and MALDI-MS of tryptic peptides.

The fractions were freeze-died and the protein concentration was determined using the Bradford method; activity was expressed in mg of protein per fraction/100 mg of crude extract. The active fraction selected for further analysis was designated f40/7841. Fractions were stored in the cold.

Example 2

In Vitro Corpus Cavernosum Assay for Smooth Muscle Relaxation

The effect of polypeptides on corpus cavernosum contractile activity in vitro was analyzed in corpus cavernosum tissue harvested from Wistar adult male rats. Tissue was vertically positioned in an isolated organ chamber under the conditions described below. Adult male Wistar rats, aged 1.5-2 months and 250-350 g in weight were sacrificed by cervical dislocation and the penis was removed from the base, yielding about 2 cm of isolated tissue. The penile tissue was dissected under a Zeiss STEMI DV4 stereoscopic magnifying glass. The tunica albuginea, which protects the cavernous and spongious corpuses, was gently removed. The cavernous bodies were removed from their central position, obtaining two fragments of equal length and diameter, which were then transferred to a Tyrode physiological solution properly oxygenated (mix of 95% $O_2$ and 5% $CO_2$), at 37° C. at pH 7.4. The composition of the Tyrode solution is shown in Table 1.

TABLE 1

Tyrode stock

| REAGENT | CONCENTRATION (mM) | MOLECULAR WEIGHT (g/mol) | STOCK FOR 2 LITER (g) |
|---|---|---|---|
| NaCl | 137.00 | 58.44 | 320.240 |
| KCl | 5.40 | 74.56 | 16.104 |
| $CaCl_2 \times 2H_2O$ | 2.70 | 147.02 | 15.818 |
| $MgCl_2 \times 6H_2O$ | 0.50 | 203.30 | 4.066 |
| $NaHCO_3$ | 11.90 | 84.01 | 39.988 |
| $NaH_2PO_4 \times H_2O$ | 0.45 | 137.99 | 2.484 |
| Glucose × $1H_2O$ | 5.55 | 198.17 | — |

The salts NaCl, $CaCl_2 \times 2H_2O$, $MgCl_2 \times 6H_2O$ and $NaHCO_3$ were purchased from Winkler-USA; KCl from Fluka Chemika-Switzerland; $NaH_2PO_4 \times H_2O$, Glucose×1 $H_2O$ from Merck-Germany.

Figure 6A:
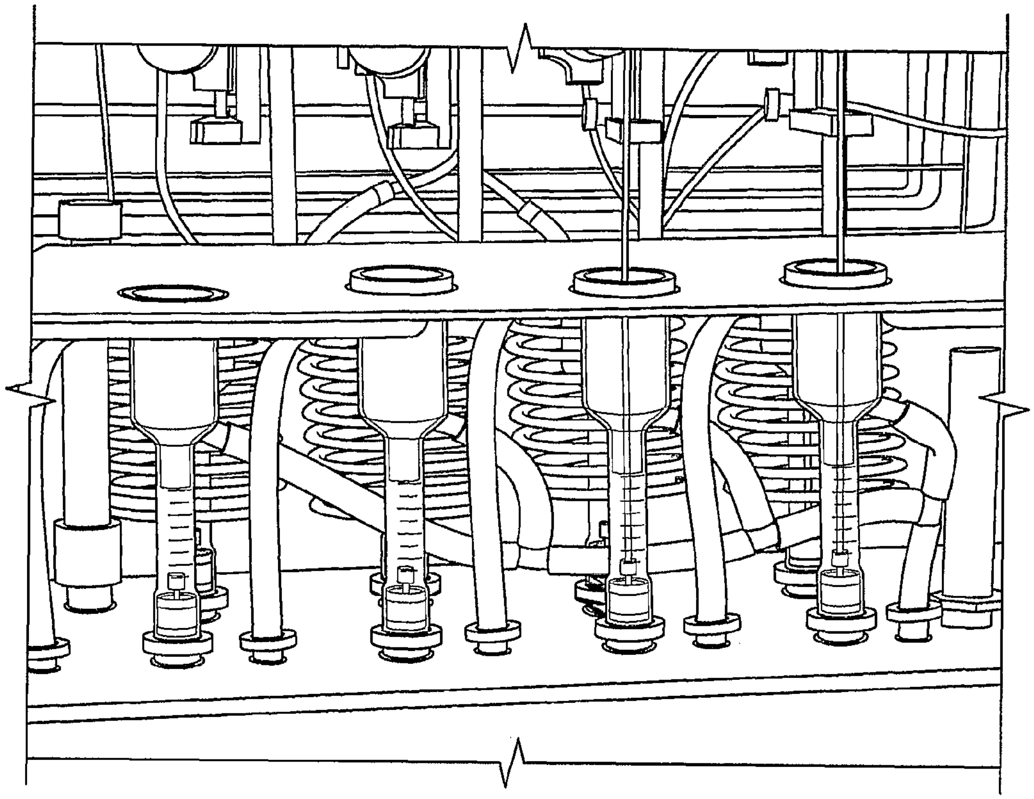
FIG. 6A shows the organ chamber used for the corpus cavernosum relaxation assay.
Figure 6B:
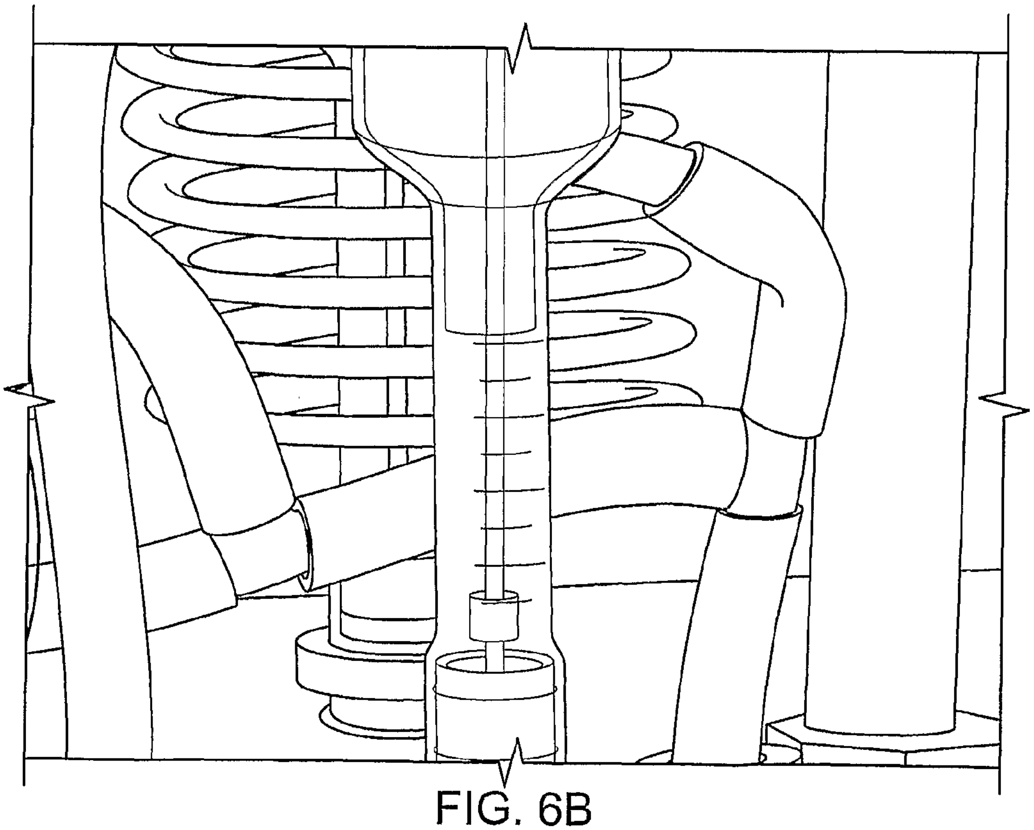
FIG. 6B shows a close-up view of a single corpus cavernosum sample in the organ chamber.

The assay was performed in a 4/5 ml LSI LETICA isolated organ chamber as shown in FIG. 6*a*, with a close-up view in FIG. 6*b*. The cavernous segments were tied with silk at their distal and proximal extremes and immersed in a Tyrode physiologic solution in the chambers. The distal part was tied to the connecting rod and the proximal portion was connected to the isometric contraction transducer (TRI 201/0-25 g) connected to an analogue/digital interphase Power Lab/4SP Ad instrument, making it possible to store and analyse the registered signals by the use of Chart 5 software. Essentially, the fragments were connected to a analogic tension transducer, which transferred its signal to a Power Lab-Letica interphase, which records, graphs and stores the information generated by the physiologic preparation in force/time (g/min scale).

Prior to assaying the polypeptides, the isolated corpus cavernosum samples were stabilized as follows. After placing the corpus cavernosum in the isolated organ chamber, a 0.5 g tension at a normal velocity (1:1 proportion) was applied for one hour. During this time the basal tension and oxygenation (10 ml/min) remained constant. After the first 20 minutes, the preparation was washed using Tyrode physiologic solution, the tension was fixed and the procedure was repeated every 20 minutes for a total of 4 times. In the final washing process, in Chart 5 control system, the recording speed was modified from 10× to 1×.

Example 3

The Effect of f40/7841 on Corpus Cavernosum Contractile Activity

Figure 7:
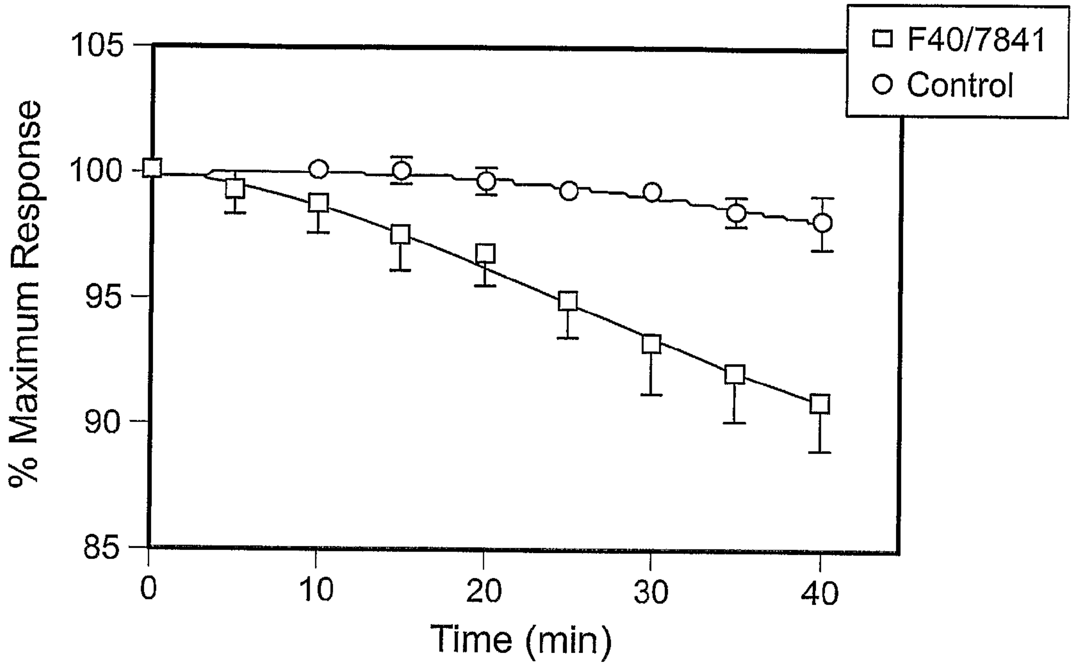
FIG. 7 depicts the results of an experiment showing the effect of the f40/7841 polypeptide on the corpus cavernosum relaxation assay.

The ability of f40/7841 to induce smooth muscle relaxation was assayed in the corpus cavernosum assay described in Example 2 in the presence of 50 μM phenylephrine, a pharmacological agonist of the alpha-adrenergic receptor that induces smooth muscle contraction. As shown in FIG. 7, treatment of corpus cavernosum with phenylephrine produced a phasic contractile response followed by a steadily maintained tonic response during the first 20 minutes that diminished slightly at later time points (circles). Addition of total extract of *Latrodectus mactans* venom at 2 μg/ml in the chamber, in the presence of fenilefrine (50 μM) resulted in a decrease in the contractile force by about 10% at 40 minutes after addition. The graph shows the results of 56 measurements.

Figure 8:
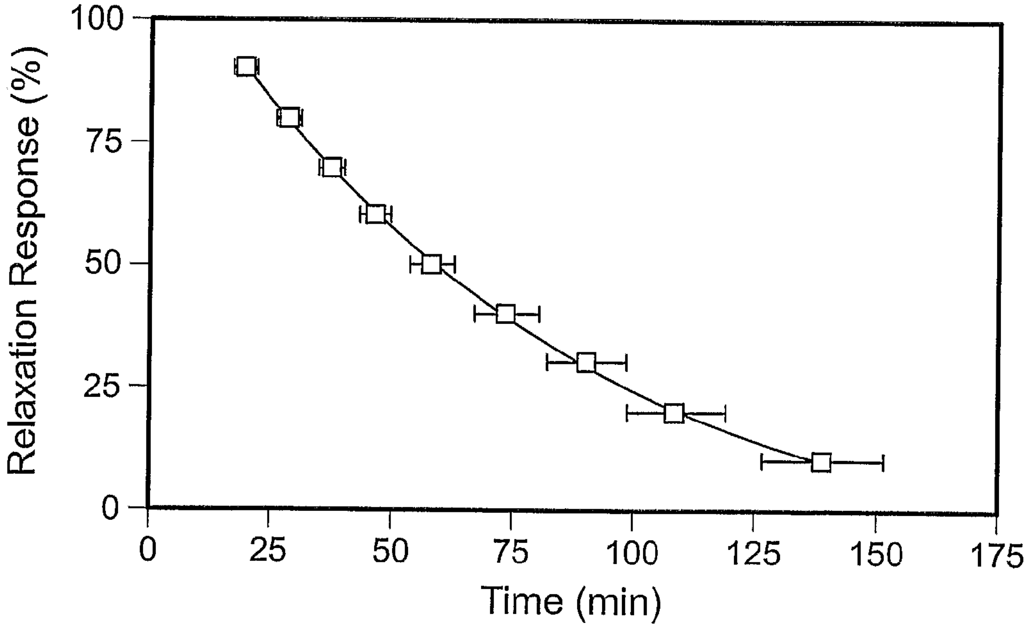
FIG. 8 depicts the results of an experiment showing the effect of the f40/7841 polypeptide on the corpus cavernosum relaxation assay in the presence of the purified fraction f40/7841 at 0.1 μg/ml.

FIG. 8 shows a similar experiment in which corpus cavernosum fragments were treated with phenylephrine as above in the presence of the purified fraction f40/7841 at 0.1 μg/ml. To determine the relaxation potential it was necessary to induce first a maximum contractile response (control), in the presence of a drug that activates α-adrenergic receptors, phenylephrine (50 μM). The obtained results of the experimental series are statistically analyzed with a statistical significance of $P<0.05$, and graphed with GraphPad Prim.V.3.02 software.

Example 4

Analogue Records of f40/7841 Relaxation Activity

Figure 9:
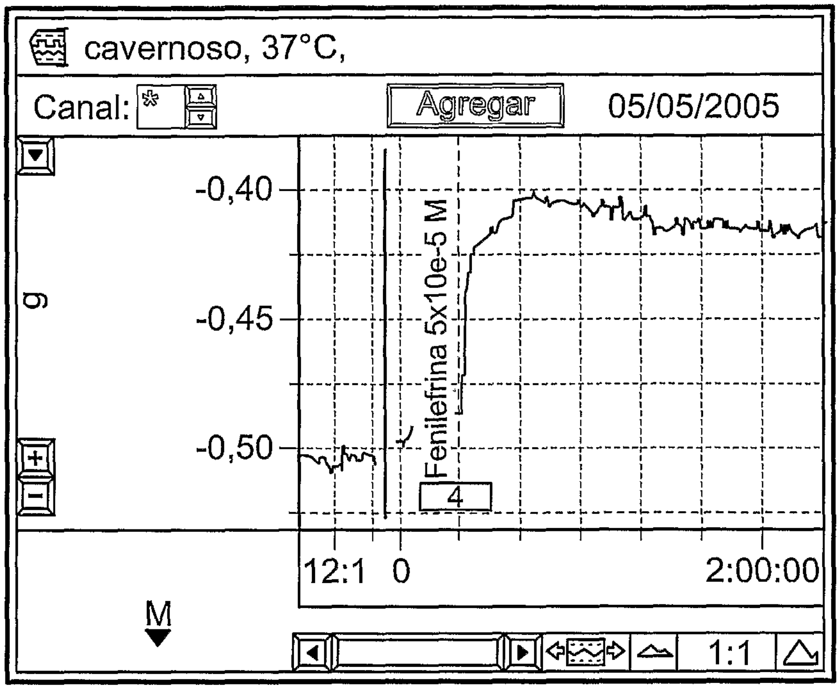
FIG. 9 depicts an analogue tracing showing the effect of phenylephrine on corpus cavernosum contractility.

A typical analogue recording of a response of a corpus cavernosum fragment contracted with 50 μM phenylephrine is shown in FIG. 9. Tissue fragments were collected as described in Example 2, placed in the organ chamber and stabilized for one hour. The basal tracing was obtained after 1 hour with an applied starting tension of 0.5 g in a physiologic environment at pH 7.4 and gas mix 95% $O_2$ and 5% $CO_2$. Following the addition of phenylephrine to a final concentration of 50 μM, a quick phasic contraction took place followed by a tonic component that was maintained over time. Instrument calibration was 0.5 g.

Figure 10:
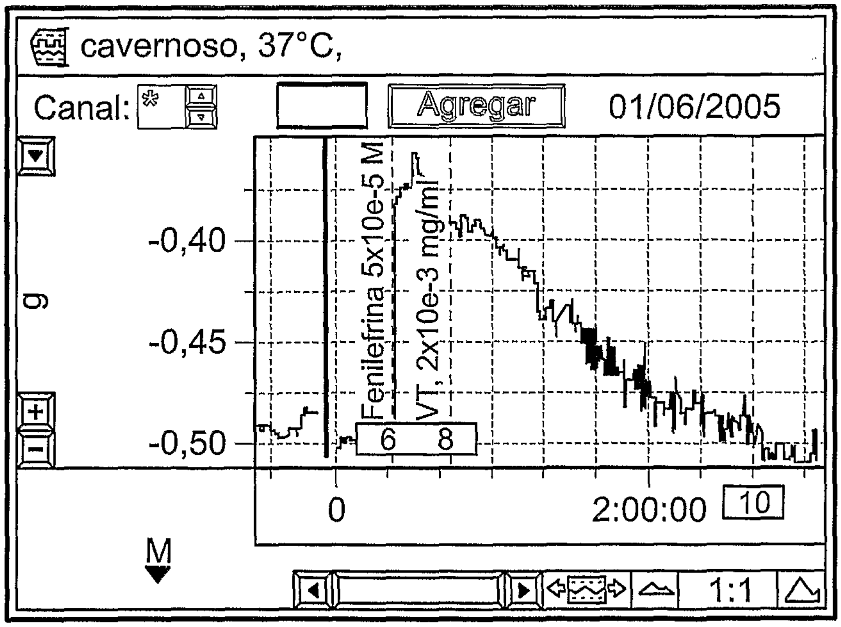
FIG. 10 depicts an analogue tracing showing the effect of the polypeptide f40/7841 on the corpus cavernosum relaxation assay.

FIG. 10 shows an analogue recording of a response of a corpus cavernosum fragment contracted with phenylephrine and the treated with the f40/7481 polypeptide. An isolated fragment of corpus cavernosum was treated with phenylephrine as above for 20 minutes followed by the addition of f40/7841 to a final concentration of 2 μg/ml. Addition of the f40/7841 polypeptide resulted in a rapid decrease in tonic contraction. Instrument calibration was 0.5 g.

Example 5

Effect of Inhibition of Nitric Oxide Synthesis on f40/7841 Activity

Figure 11:
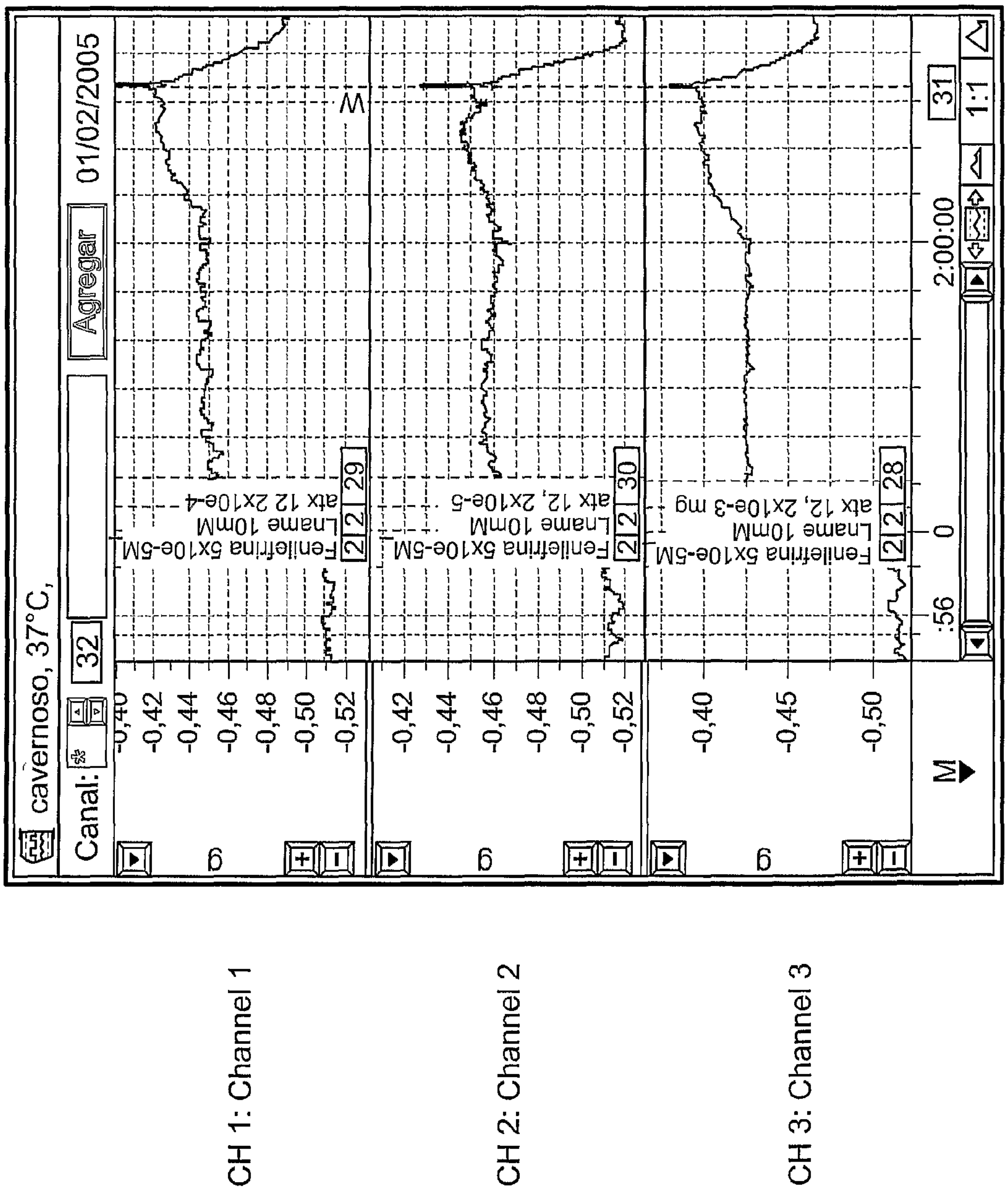
FIG. 11 depicts analogue tracings from an experiment analyzing the effect of f40/7841 on the corpus cavernosum relaxation assay in the presence of L-NAME, an agent that blocks NO production.

The role of nitric oxide in f40/7841 relaxation activity was explored by treating corpus cavernosum samples with the nitric oxide synthase inhibitor, N-nitro-L-arginine methyl ester (L-NAME). Contraction of corpus cavernosum fragments was induced with phenylephrine as in Example 4 for 10 minutes, followed by the addition of L-NAME to a final concentration of 10 mM. After an additional 10 minutes, the f40/7481 polypeptide was added. Analogue tracings are shown in FIG. 11. CH-1=phenylephrine 5 μM+L-NAME 10 mM+F40/7841 0.2 μg/ml; CH-2=phenylephrine 5 μM+L-NAME 10 mM+F40/7841 0.02 μg/ml; and CH-3=phenylephrine 5 μM+L-NAME 10 mM+F40/7841 2 μg/ml. As was the case for Example 4, the addition of phenylephrine resulted in a rapid contraction of the corpus cavernosum tissue; in the presence of the nitric oxide inhibitor, the f40/7481 polypeptide did not induce a decrease in contraction, i.e., L-NAME blocked the ability of f40/7481 to relax contracted tissue. The instrument calibration is 0.5 g.

Figure 12:
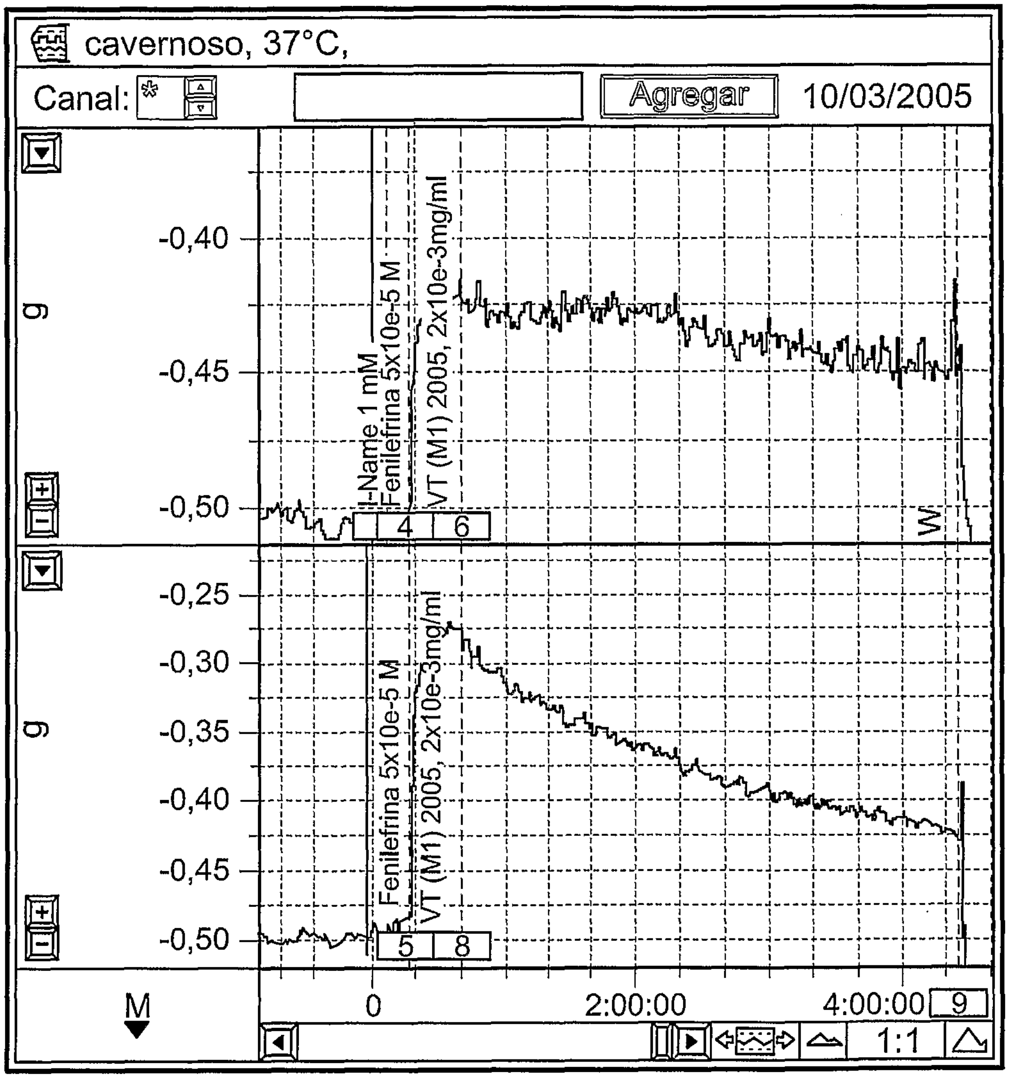
FIG. 12 depicts analogue tracings from an experiment analyzing the effect of f40/7841 on the corpus cavernosum relaxation assay in the presence of L-NAME, an agent that blocks NO production.

FIG. 12 shows a similar experiment in which corpus cavernosum fragments were treated with phenylephrine followed by the addition of f40/7481 polypeptide in the presence (upper tracing) and absence (lower tracing) of L-NAME. As was the case for the experiment shown in FIG. 11, inhibition of nitric oxide synthase abolished the ability of the f40/7481 polypeptide to induce corpus cavernosum relaxation.

Example 6

Effect of Atropine on f40/7841 Relaxation Activity

Figure 13:
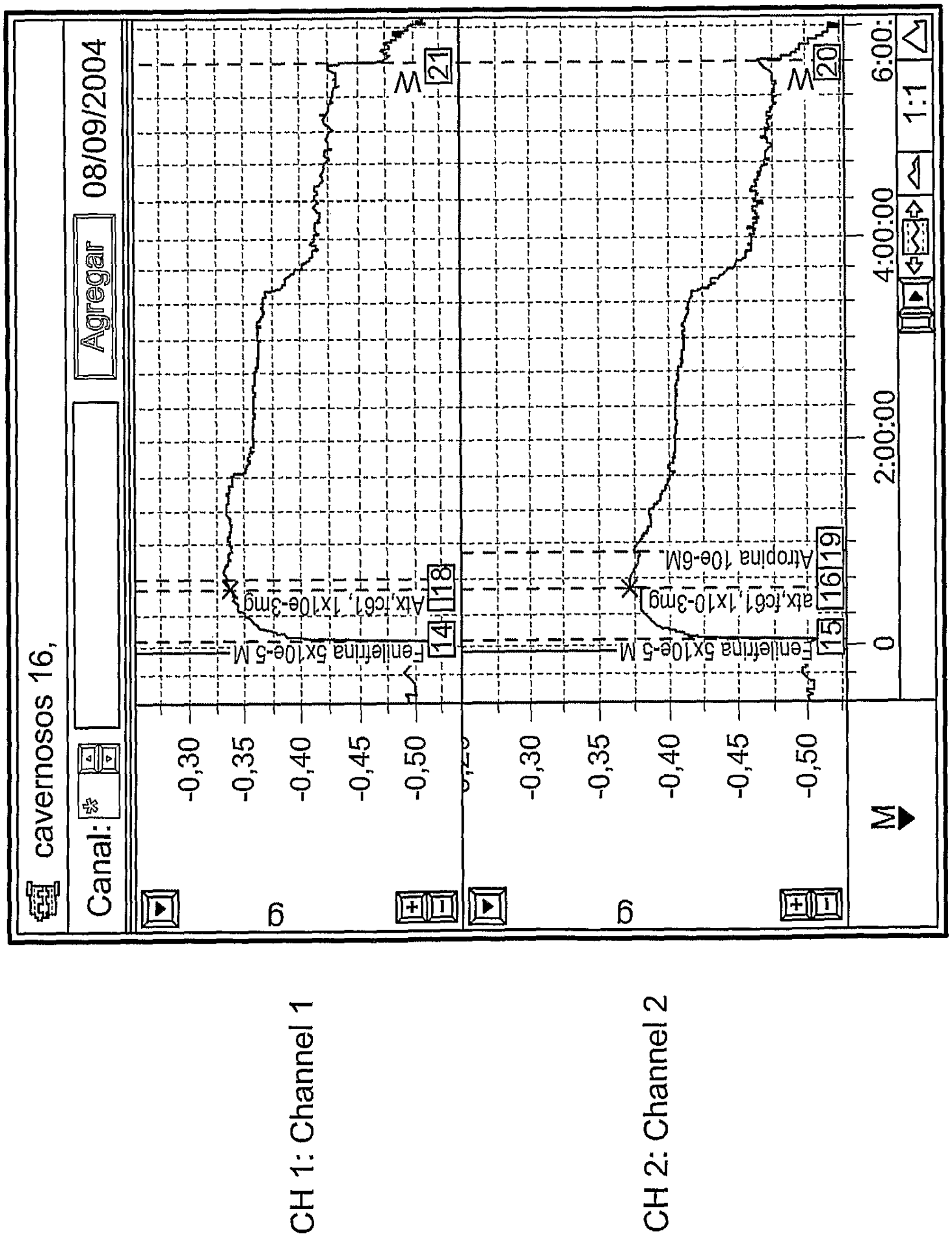
FIG. 13 depicts analogue tracings from an experiment analyzing the effect of f40/7841 on the corpus cavernosum relaxation assay in the presence of the α-adrenergic agonist, atropine.

The role of the acetylcholine receptor in f40/7841 relaxation activity was explored by treating corpus cavernosum samples with the muscarinic acetylcholine receptor antagonist, atropine. The results of this experiment are shown in FIG. 13. CH-1=Phenylephrine 5 μM+Atropine 1 μM+F40/7841 1 μgml; CH-2=Phenylephrine 5 μM+F40/7841 1 μgml+Atropine 1 μM. Contraction of corpus cavernosum fragments was induced with phenylephrine as in Example 4 for 40 minutes, followed by the addition of atropine to a final concentration of 1 uM (upper tracing). The tonic response was gradually reduced over time in the presence of atropine. The sample in the lower tracing also received the addition of f40/7481 polypeptide; the ability of the f40/7481 polypeptide to induce relaxation was attenuated in the presence of atropine.

Figure 14:
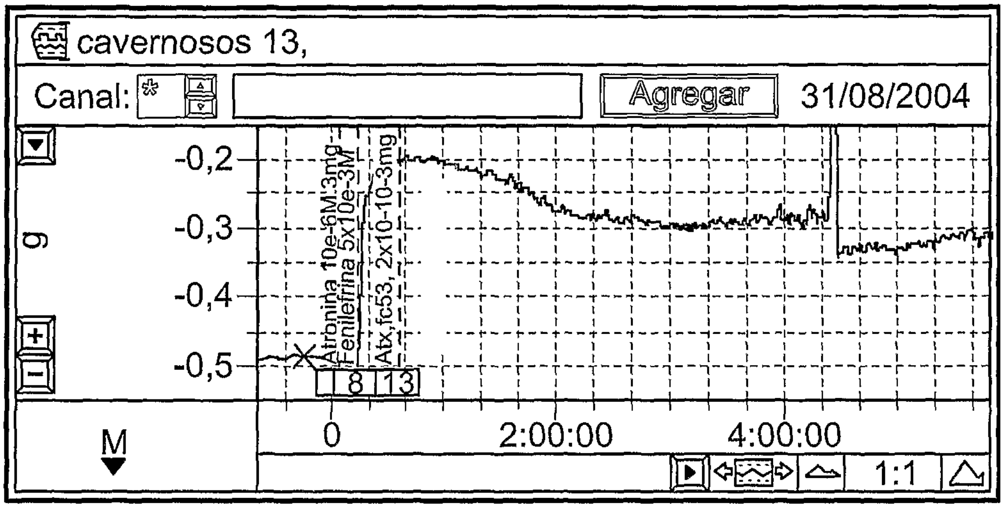
FIG. 14 depicts analogue tracings from an experiment analyzing the effect of f40/7841 on the corpus cavernosum relaxation assay in the presence of the α-adrenergic agonist, atropine.

Similar results were obtained when atropine was added prior to the phenylephrine. In the experiment shown in FIG. 14, corpus cavernosum samples were prepared according to Example 4, stabilized for one hour and then incubated in 1 μM atropine followed by the addition of phenylephrine to a final concentration of 50 μM. The typical rapid contractile response following phenylephrine addition was observed. Twenty minutes after phenylephrine addition, f40/7481 polypeptide was added to a final concentration of 2 μg/ml. As was the case for the experiment shown in FIG. 13, the ability of the f40/7481 polypeptide to induce relaxation was attenuated in the presence of atropine. The instrument calibration was 0.5 g.

Example 7

Activation of Nicotinic Acetylcholine Receptors (nAChR) in Transfected PC12 Cells by f40/7841

The ability of the f40/7841 polypeptide to activate nicotinic acetylcholine receptors (nAChR) was assayed by whole cell patch clamp analysis of PC12 cells that had been engineered to express the alpha 7 nicotinic acetylcholine receptor ($\alpha_7$nAch). PC12 cells were transfected and cultured for 48 hours in an 80% of MEM, solution that contained (mM): 150 NaCl, 5.4 KCl, 2.0 $CaCl_2$, 1.0 $MgCl_2$, 10 glucose and 10 Hepes (7.4), 2 mM, and 10% of fetal bovine serum at 37° C. (Trifaro et al. *In vitro Cell Dev. Biol.* 1990). The cells were incubated for one hour at 22° C. before starting the experiments. The current changes were detected through a whole-cell patch-clamp system through a Warner PC-501[a] amplifier and an inverted Olympus 9° 70 microscope. The membrane potential was adjusted to −60 mV; the current was recorded at intervals of 5 μs and it was filtered at 2 Kh using a computer connected to a recording system through an acquisition card Digidata 9.0 (Axon Instrument, Inc) and the software PC 9 (Axon Instrument, Inc). The stock solution for the assays with the peptides were kept refrigerated at 4° C. and the micropipettes contained an internal solution of: 140 mM NaCl, 5 mM KCl, 2 mM $CaCl_2$, 1.5 mM $MgCl_2$, and 10 mM HEPES, pH 7.4.

The purified f40/7841 polypeptide was purified according to the method in Example 1. 0.1 mg of the polypeptide was diluted in 100 μl. of sterile PBS at pH 7.4. The diluted polypeptide was dispersed in 25 μl aliquots in Eppendorf tubes and kept refrigerated at −20° C. All manipulations of the peptide were carried out under a laminar flow hood.

Borosilicate capillaries with BF150-117-15 filaments were used. The capillaries were handled in original containers and the ends were polished with a BF150-117-15 equipment to provide maximum membrane adhesion against negative pressure. The tip diameters were approximately 1 μm and the resistance was of 5-8 MΩ. The capillaries were subject to visual inspection before use.

For whole cell patch clamp analysis, the cells were carefully touched using micromanipulators through negative suction or pressure; seal formation was noted as an increase in the electric resistance. When the equipment was in 0V, 10 mV are generated, observing in a virtual microscope integrated to the program of the equipment in the screen of the computer, a pulse or variable amplitude current. This square-shaped pulse was a reflection of the resistance between the environment and the electrode. When touching the cell, the current decreased and the amplitude of the square-shaped pulse was significantly reduced. This change in the oscilloscope showed that the tip had touched the membrane and that the electric conditions changed as a result of the development of resistance.

Figure 15:
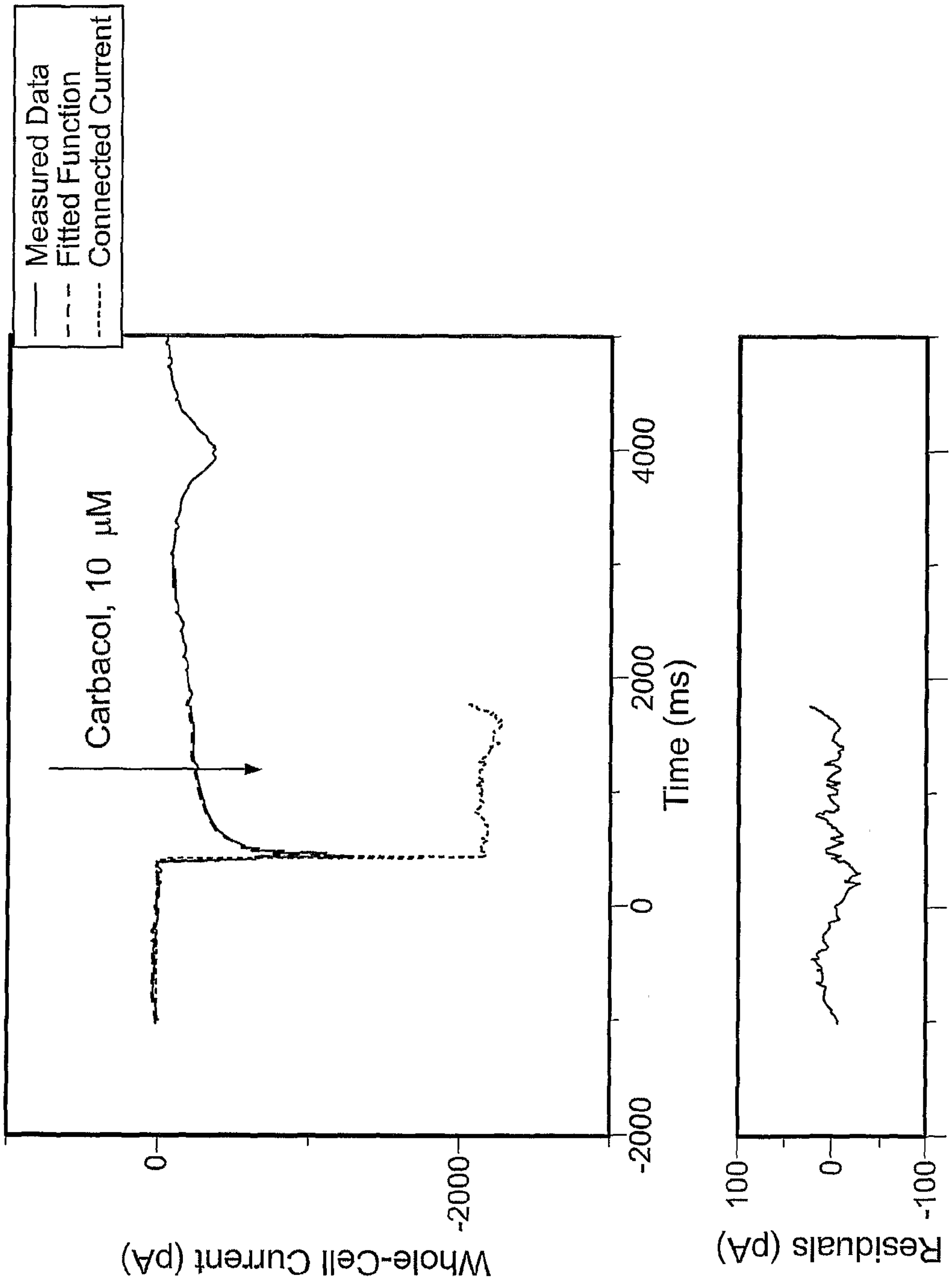
FIG. 15 depicts the results of a whole-cell patch clamp experiment analyzing the effect of the α7-nicotinic acetylcholine receptor agonist, carbachol, on potassium channel activation in PC12 cells engineered to express the α7-nicotinic acetylcholine receptor.

The electrophysiological response induced by nicotinic channel activation in the presence of a positive control compound, 10 μM carbachol, a cholinergic agonist, is shown in FIG. 15. As shown in the upper tracing, carbachol treatment of αn7AchR transfected PC12 cells resulted in a rapid induction of a potassium current of 10 pA, followed by a tailing current. The graph also shows that the capacitive current was not modified during the experiment, indicating that the preparation that did not lose resistance and that the seal of the cell membrane was maintained during the recording period.

Figure 16:
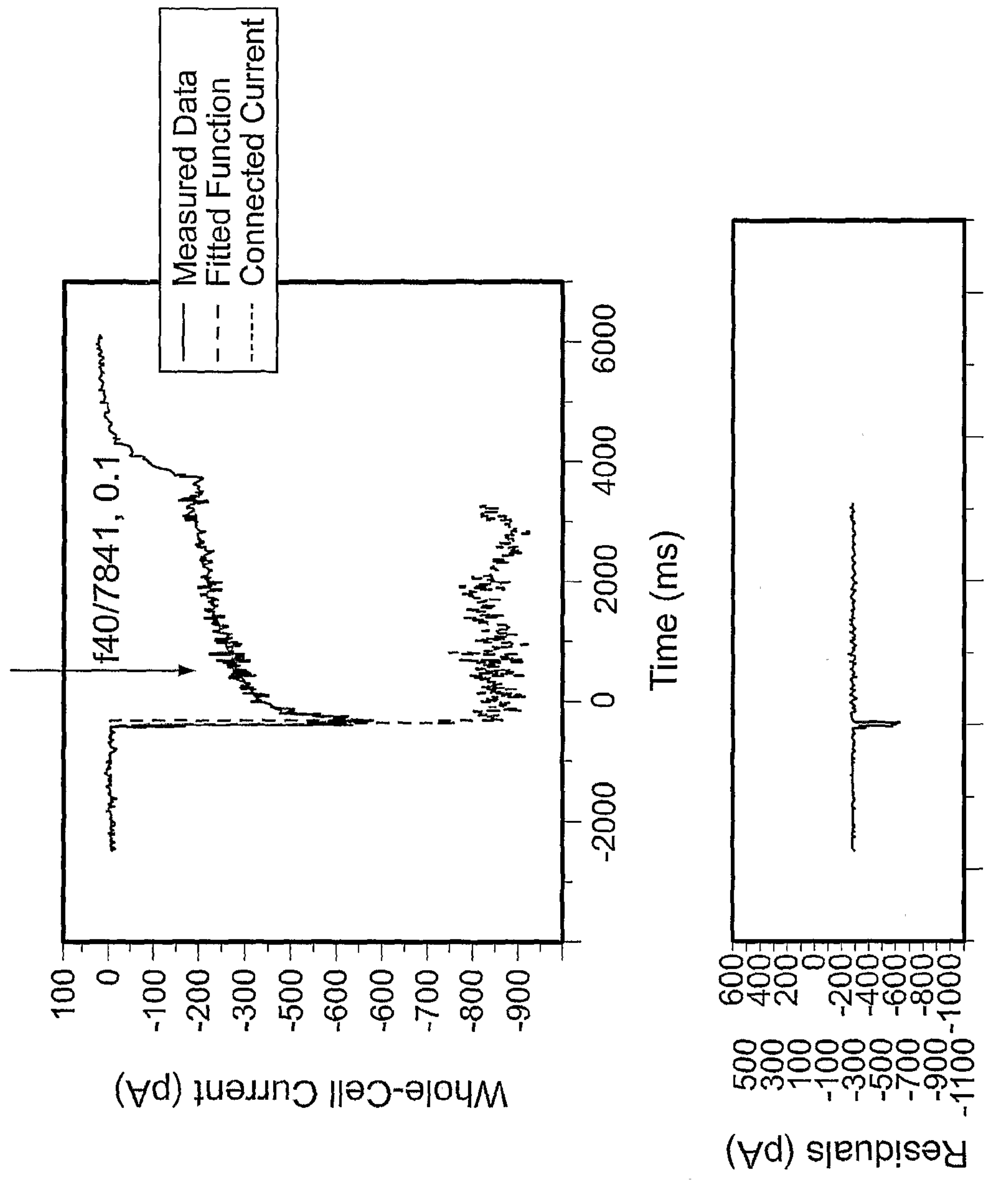
FIG. 16 depicts the results of a whole-cell patch clamp experiment analyzing the effect of the polypeptide f40/7841 in the presence of the α7-nicotinic acetylcholine receptor agonist, carbachol, on potassium channel activation in PC12 cells engineered to express the α7-nicotinic acetylcholine receptor.

The electrophysiological response induced by nicotinic channel activation in the presence of the polypeptide f40/7841 is shown in FIG. 16. The f40/7841 polypeptide at a concentration of 0.1 μg/ml acted as an synergic-pharmacological agonist on the preparation, producing a rapid potassium current of 500 pA, followed by a tailing current. The lower graph showed that the capacitive current was not modified during the experiment, indicating that the preparation that did not lose resistance and that the seal of the cell membrane was maintained during the recording period. The data in FIG. 16 indicated that the f40/7841 polypeptide induced a specific cholinergic activity (α7nAch), i.e., a potassium current that blocked a calcium current to the intracellular environment.

Example 8

Determination of Intracellular Calcium Concentration

To confirm that the f40/7841 polypeptide had no effect on calcium flux, C2C12 myoblasts were treated with f40/7841 polypeptide and intracellular calcium levels were assayed using the calcium-sensitive fluorchrome, Fluo-3AM. For the intracellular $Ca^{2+}$ measurements, a Confocal LSM 510 Meta Confocal (Zeiss, Jena, Alemania) microscope with a lasing line excitation of 488 nm was used. C2C12 cells were seeded in 60 mm culture dishes (Nalge Nunc International, Rochester, N.Y.) and cultured for 48 hours at which time each plate contained about 250,000 cells. The cells were loaded with fluorochrome in concentration of 4 μM fluo-3AM (Sigma) in 0.5% $Me_2SO$ and 0.1% of pluronic acid F-127 for 30 minutes at 37° C.; washed three times with a modified Dulbecco's solution with 10% of fetal bovine serum and returned to the incubator.

The fluorescence of Fluo-3AM was stimulated at 488 nm and measured at 515 nm using a bandpass filter. The intracellular $Ca^{2+}$ was measured for 10 seconds, followed by the addition of 1 μM f40/7841 polypeptide and 1.5 mM of carbachol. The $Ca^{2+}$ changes were monitored for 2 minutes and the images were taken every 1.5 sec. The calcium ionophore 4-Br-A23187 (5 μM) followed by 10 mM EGTA were then added to obtain the maximum calcium excitation (Fmax) and the minimum fluorescence (Fmin), respectively. The intracellular $[Ca^{2+}]$ of fluorescence (F) obtained by the used f40/7841 was calculated in the following way: intracellular $[Ca^{2+}]$=Kd*(*F−F*min)/(*F*max−*F*), assuming 450 nM. *Kd* for the fluo-3AM, the concentrations were calculated in cellular populations that contained at least 10 cells.

Figure 17:
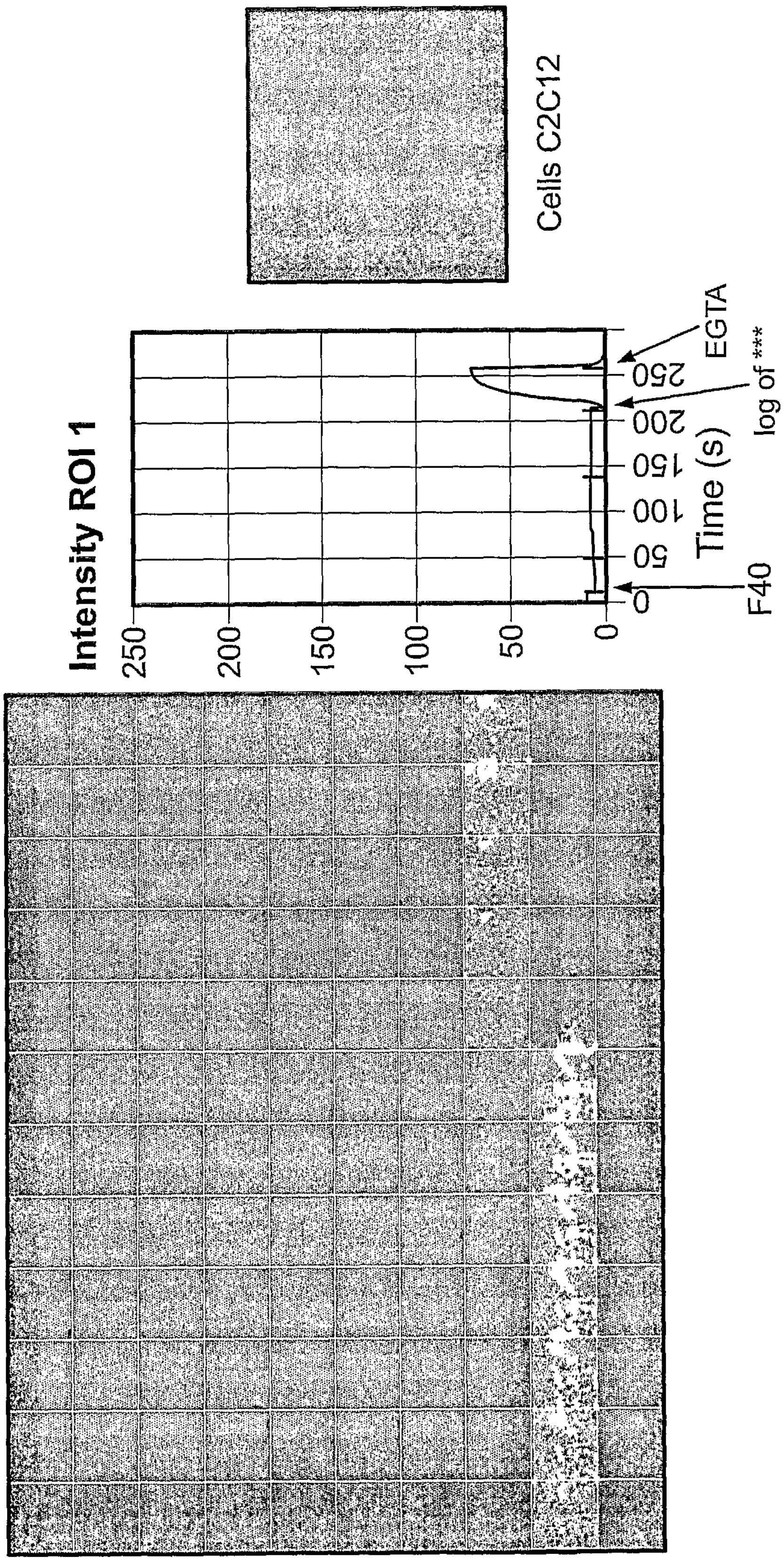
FIG. 17 shows a photoimage of C2C12 cells that had been loaded with the fluorchrome, fluo-3AM (right and left panels) and a graph (center panel) depicting the effect of the f40/7841 polypeptide, the calcium ionophore, 4-Br-A23187, and the calcium chelator, EGTA on calcium flux.

A photoimage of C2C12 cells activated by the f40/7841 polypeptide is shown in at the left side of FIG. 17; sequential images were taken every 10 msec. As shown in the graph in the center of FIG. 17, the f40/7841 polypeptide did not induce calcium flux in C2C12 cells. Addition of the positive control compound, the calcium ionophore 4-Br-A23187 resulted in a sharp spike of fluorescence which was abolished by the addition of the calcium chelator, EGTA.

Example 9

Synergistic Effect of Sildenafil Citrate and f40/7481

Contraction of corpus cavernosum fragments was induced with 50 μM phenylephrine according to the method described in Example 2. As shown in FIG. 1, the subsequent addition of sildenafil citrate (▲ triangles) to a final concentration of 1 μM resulted in a slow decrease of the contractile response over a period of 25-30 minutes. Co-addition of f40/7841 (■ squares) to a final concentration of 2 μg/ml resulted in a significant decrease in the contractile response when compared to sildenafil citrate alone. Moreover, typically a concentration of 100 μM of sildenafil citrate alone was required to observe a relaxation rate comparable to that seen with f40/7841 polypeptide and only 1 μM sildenafil citrate, suggesting that the f40/7841 polypeptide can significantly enhance the action of sildenafil.

Example 10

Design of RT-PCR Primers for Analysis of *Latrodectus mactans* RNA

In order to isolate nucleic acids encoding the f40/7481 polypeptide from the Chilean species, *Latrodectus mactans*, primers were designed based on the sequence of the latrotoxin of the Euroasiatic subspecies, *Latrodectus tredecimguttatus*. DNA primers were chosen based on the conserved region in LOCUS DQ011856. The primer sequences were as shown below:

```
                                          (SEQ ID NO: 4)
Sense:      aTX1F: 5'-GTTGCTGGTCAGGACTCTCTGG-3

                                          (SEQ ID NO: 5)
Antisense:  aTX1R: 5'-TTTGGCCTCTTCTAAATCTTTTACG-3'

                                          (SEQ ID NO: 6)
Sense:      aTX2F: 5'-GCTTAAGCTTATCTGCATTGCCT-3'

                                          (SEQ ID NO: 7)
Antisense:  aTX2R: 5'-GACAACACCTTCCTTATGCAAATCTT
            C-3'.
```

Figure 2:
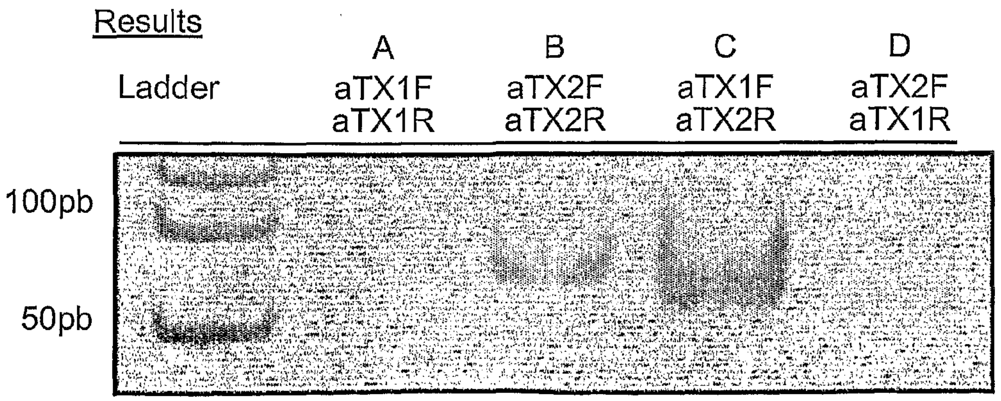
FIG. 2 depicts the results of an RT-PCR assay to identify useful primer pairs for amplification of α-latrotoxin mRNA from *Latrodectus mactans.*
Figure 3:
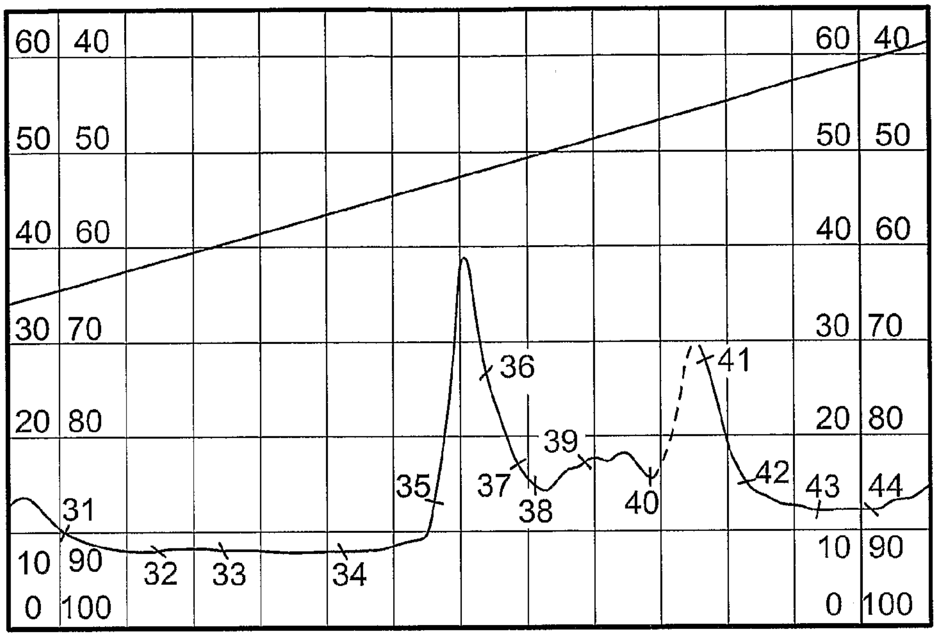
FIG. 3 depicts the chromatographic profile of a crude extract from 4500 *L. mactans* venom glands.

These primers were used for RT-PCR on mRNA extracted from the Chilean spider, *Latrodectus mactans*. As shown in FIG. 2, all but one of the combinations of primers gave a single fragment; the strongest signal was obtained using the aTX1F and the aTX2R primers.

Example 11

Prophetic Example of In Vivo Assay

In Vivo Assay of ED:

Rodents and other mammals typically used in laboratory studies can be used to assess the present compositions. For example, one can prepare a pharmaceutically acceptable composition including a polypeptide having or including the sequence of SEQ ID NO:1 and administer it (by, for example, subcutaneous or intraperitoneal injection) into male Fisher 344 rats. If desired, parallel studies can be carried out with young (~4 months old) and aged (~19 months old) rats as described in Musicki et al. (*J. Urology* 174:1493-1496, 2003). Saline or "vehicle only" control experiments can be conducted in parallel. Erection can be assessed visually and the studies can be configured to further assess refraction. For example, the compositions can be administered routinely (e.g., 1-3 times per day) for a period of time (e.g., 2-4 weeks) and electrical stimulation of the cavernous nerve can be performed to assess penile erection after a washout period.

Example 12

Prophetic cDNA Cloning of the mRNA Encoding SEQ ID NO:1

An α-latrotoxin cDNA clone from *L. mactans* is obtained using standard molecular biology methods (see, for example, Molecular Cloning: A Laboratory Manual (Third Edition) J. Sambrook, P. MacCallum, D. Russell, CSHL Press, Cold Spring Harbor, N.Y.). Briefly, the PCR product obtained in the experiment described in Example 10 is cloned and sequenced and the DNA sequence is aligned with the α-latrotoxin of the Euroasiatic subspecies, *Latrodectus tredecimguttatus* as well as DNA sequences from other α-latrotoxins to confirm that the primers have annealed with α-latrotoxin mRNA. If the sequence is homologous with or identical to the *L. tredecimguttatus*, the full length cDNA clone is obtained in either of two ways. Additional sets of overlapping primers are designed to generate longer PCR products using a variety of PCR-based methods, including for example, inverse PCR, RACE, followed by isolation of the PCR fragments and direct cloning, using for example, commercially available systems such as the QIAgen PCR cloning kit. Alternatively, an *L. mactans* cDNA library is constructed and the cloned sequence is used to probe the library; the clones identified are sequenced to confirm their identity. Regardless of the method that is used, the clones are sequenced to confirm that a full-length cDNA sequence has been isolated.

The resulting cDNA sequence is then inserted into any vector system useful for protein expression, for example, pET28 (Stratagene) which has a T7 RNA polymerase promotor. The resulting plasmids are used to transform BL21 bacteria (Strategene) using a BIORAD electroporator. Transformants are cultured in 2× YT to an optical density of 2.0, then protein synthesis is induced with 1 nM IPTG for 3 h at 37° C. The bacterially expressed protein is purified according to the HPLC method in Example 1.

What is claimed is:

1. A purified polypeptide comprising an amino acid sequence that is at least 95% identical to SEQ ID NO:1 and with one or more amino acid substitutions relative to SEQ ID NO:1.

2. The polypeptide of claim 1, wherein the one or more amino acid substitutions comprise one or more conservative amino acid substitutions.

3. A pharmaceutically acceptable composition comprising the polypeptide of claim 1.

4. The pharmaceutically acceptable composition of claim 3, wherein the one or more amino acid substitution comprise one or more conservative amino acid substitutions.

5. A pharmaceutically acceptable composition comprising the polypeptide of claim 1, wherein the amino acid sequence comprises a heterologous sequence.

6. A pharmaceutically acceptable composition comprising a purified polypeptide comprising an amino acid sequence that is at least 95% identical to SEQ ID NO:1 and a second pharmaceutically active ingredient, wherein the second pharmaceutically active ingredient is sildenafil citrate.

* * * * *

SEQUENCE LISTING

```
<160> NUMBER OF SEQ ID NOS: 6

<210> SEQ ID NO 1
<211> LENGTH: 69
<212> TYPE: PRT
<213> ORGANISM: Artificial Sequence
<220> FEATURE:
<223> OTHER INFORMATION: Synthetically generated peptide from Chilean
      Latrodectus mactans

<400> SEQUENCE: 1

Gly Asp Ser Leu Asp Pro Ala Glu Phe Ala Cys Ala Asp Asp Ile Asp
1               5                   10                  15

Gln Ala Glu Leu Leu Lys Asn Asn Asp Ile Cys Leu Gln Cys Glu Asp
            20                  25                  30

Leu His Lys Glu Gly Leu Val Phe Ser Leu Cys Lys Thr Asn Cys Phe
        35                  40                  45

Ser Thr Glu Tyr Phe Gln His Cys Val Lys Asp Leu Glu Glu Ala Lys
    50                  55                  60

Lys Glu Pro Pro Glu
65


<210> SEQ ID NO 2
<211> LENGTH: 88
<212> TYPE: PRT
<213> ORGANISM: Latrodectus tredecimguttatus

<400> SEQUENCE: 2

Met Leu Lys Leu Ile Cys Ile Ala Phe Leu Val Thr Val Leu Thr Leu
1               5                   10                  15

Val Ala Gly Gln Asp Ser Leu Asp Pro Ala Glu Phe Gly Cys Ala Asp
            20                  25                  30

Asp Val Asn Gln Ala Glu Leu Leu Lys Asn Asn Asp Ile Cys Leu Gln
        35                  40                  45

Cys Glu Asp Leu His Lys Glu Gly Val Val Phe Ser Leu Cys Lys Thr
    50                  55                  60

Asn Cys Phe Thr Thr Glu Tyr Phe Gln His Cys Val Lys Asp Leu Glu
```

-continued

```
65                  70                  75                  80

Glu Ala Lys Lys Glu Pro Pro Glu
                85


<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3

gttgctggtc aggactctct gg                                              22


<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

tttggcctct tctaaatctt ttacg                                           25


<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5

gcttaagctt atctgcattg cct                                             23


<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6

gacaacacct tccttatgca aatcttc                                         27
```